(12) United States Patent
Ciccone et al.

(10) Patent No.: US 12,372,508 B2
(45) Date of Patent: Jul. 29, 2025

(54) ALIGNMENT TOOL FOR OPEN-PATH GAS DETECTORS

(71) Applicant: MSA TECHNOLOGY, LLC, Cranberry Township, PA (US)

(72) Inventors: Nicholas Emidio Ciccone, Allison Park, PA (US); Mark Hall, Cranberry Township, PA (US)

(73) Assignee: MSA Technology, LLC, Cranberry Township, PA (US)

( * ) Notice: Subject to any disclaimer, the term of this patent is extended or adjusted under 35 U.S.C. 154(b) by 568 days.

(21) Appl. No.: 17/728,276

(22) Filed: Apr. 25, 2022

(65) Prior Publication Data
US 2023/0341368 A1     Oct. 26, 2023

(51) Int. Cl.
G01N 33/00 (2006.01)
(52) U.S. Cl.
CPC ..... G01N 33/0062 (2013.01); G01N 33/0073 (2013.01)
(58) Field of Classification Search
CPC .......... G01N 33/0062; G01N 33/0073; G01N 2021/3513; G02B 7/004; G02B 23/02; G02B 27/62
See application file for complete search history.

(56) References Cited

U.S. PATENT DOCUMENTS 3,620,149 A * 11/1971 Ogihara ................. G03B 17/14
396/533
3,906,534 A      9/1975 Shirasaki
4,003,068 A * 1/1977 Hashimoto ............ G03B 17/14
396/71

(Continued)

FOREIGN PATENT DOCUMENTS

GB           2531959 A  *  5/2016   ......... B29C 33/3857
WO       2023211598        11/2023

OTHER PUBLICATIONS

MSA Operating Manual, Senscient ELDS 1000/2000 Series, 2019, pp. 71-83.

(Continued)

*Primary Examiner* — Mohamed K Amara
(74) *Attorney, Agent, or Firm* — BARTONY & ASSOCIATES LLC

(57) ABSTRACT

An alignment tool for use in connection with an open path gas detection system, which includes an interface including one or more connectors, includes an optical system having a scope and an attachment system operatively connected to the optical system. The attachment system includes a body including one or more cooperating connectors. The body is rotatable about an axis thereof in a first direction to bring the one or more cooperating connectors into connection with the one or more connectors. The attachment system further includes one or more locking elements which engage the one or more connectors after a predetermined amount of rotation of the body in the first direction to form a state of locked engagement. A release member is in rotatable connection with the body in a second direction, opposite the first direction, to cause the one or more locking elements to disengage from the one or more connectors of the interface so that the body can be rotated in the second direction to remove the attachment system from connection with the interface.

25 Claims, 15 Drawing Sheets

(56) References Cited

U.S. PATENT DOCUMENTS

| | | | | |
|---|---|---|---|---|
| 4,063,264 A * | 12/1977 | Ando | G03B 17/14 | 396/531 |
| 4,230,403 A * | 10/1980 | Hashimoto | G03B 17/14 | 396/298 |
| 4,247,190 A * | 1/1981 | Hashimoto | G03B 17/12 | 396/530 |
| 4,251,134 A * | 2/1981 | Sato | G03B 17/14 | 396/529 |
| 4,281,916 A * | 8/1981 | Aoyagi | G03B 17/14 | 396/298 |
| 4,299,470 A * | 11/1981 | Shimizu | G03B 17/14 | 359/826 |
| 4,320,951 A * | 3/1982 | Kawai | G03B 17/14 | 396/529 |
| 4,322,154 A * | 3/1982 | Hashimoto | G03B 17/14 | 396/505 |
| 4,326,789 A * | 4/1982 | Aoyagi | G03B 17/14 | 359/825 |
| 4,330,192 A * | 5/1982 | Shimizu | G03B 9/07 | 396/505 |
| 4,336,991 A * | 6/1982 | Isobe | G03B 17/14 | 396/298 |
| 4,451,131 A * | 5/1984 | Shimizu | G02B 7/14 | 396/505 |
| 4,461,544 A * | 7/1984 | Isobe | G02B 7/282 | 359/698 |
| 4,553,817 A * | 11/1985 | Ando | G02B 7/10 | 359/825 |
| 4,600,277 A * | 7/1986 | Murray, Jr. | G02B 23/125 | D16/132 |
| 5,012,264 A * | 4/1991 | Nagano | G03B 17/14 | 396/303 |
| 5,041,858 A * | 8/1991 | Yamamichi | G03B 17/14 | 396/532 |
| 5,590,484 A * | 1/1997 | Mooney | F41G 1/16 | 42/111 |
| 5,928,137 A * | 7/1999 | Green | A61B 90/36 | 600/106 |
| 9,798,101 B1 * | 10/2017 | Weidner | G02B 7/02 | |
| 9,945,637 B1 * | 4/2018 | Lasslo | G02B 27/34 | |
| 10,036,892 B1 * | 7/2018 | Yoon | B29D 11/00403 | |
| 10,748,401 B2 | 8/2020 | Oertel | | |
| 11,353,681 B2 * | 6/2022 | Heiser | G03B 17/14 | |
| 2004/0236285 A1 * | 11/2004 | Fisher | A61M 5/3158 | 604/207 |
| 2011/0102893 A1 * | 5/2011 | Solyar | G02B 7/004 | 359/503 |
| 2011/0149422 A1 * | 6/2011 | Sugita | G03B 13/34 | 359/824 |
| 2011/0290853 A1 * | 12/2011 | Shelton, IV | A61B 17/07207 | 227/177.1 |
| 2015/0124336 A1 * | 5/2015 | Kaufman | G01J 3/36 | 359/728 |
| 2018/0035109 A1 * | 2/2018 | Fiebig | H04N 17/02 | |
| 2021/0018733 A1 * | 1/2021 | Volfson | G02B 7/021 | |
| 2021/0215458 A1 * | 7/2021 | Theisinger | F41G 1/30 | |
| 2024/0241362 A1 * | 7/2024 | Huynh | G02B 17/023 | |

OTHER PUBLICATIONS

Honeywell, Technical Handbook, Searchline Excel, Infrared Gas Detectors, Issue 12—Oct. 1, 2012.

Honeywell, Technical Manual, Searchline Excel Plus, Searchline Excel Edge, Open Path Flammable Hydrocarbon gas Detector, Chapter 7, Jul. 2021, pp. 41-47.

Det-Tronics, FlexSight LS2000 Line-of Sight, Infrared Hydrocarbon Gas Detector, May 2020, pp. 25-27.

\* cited by examiner

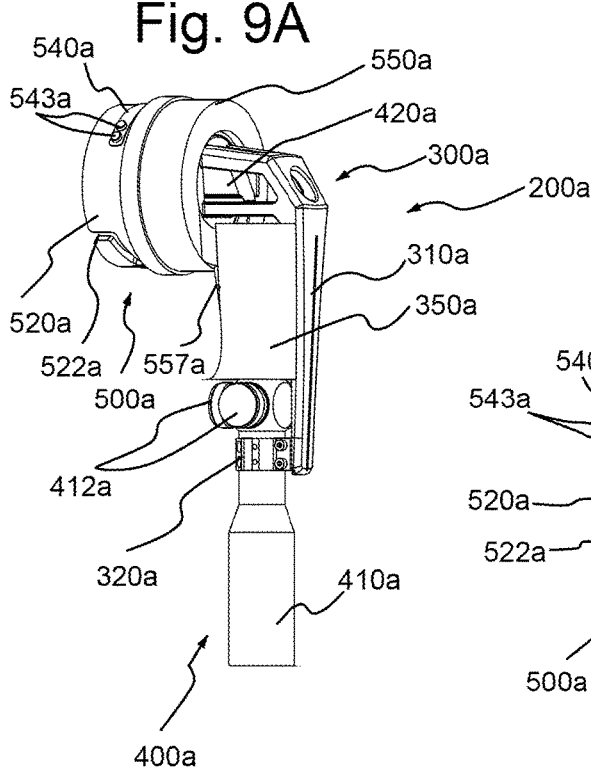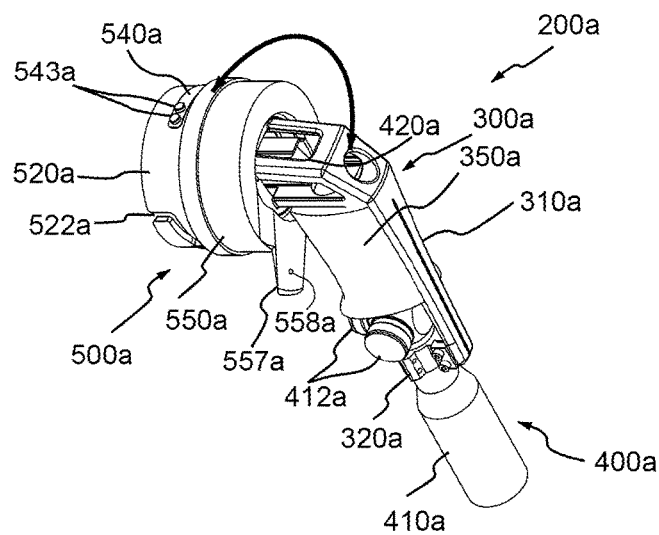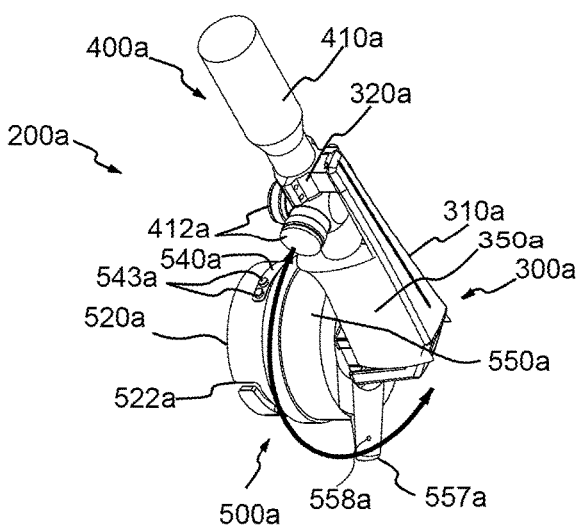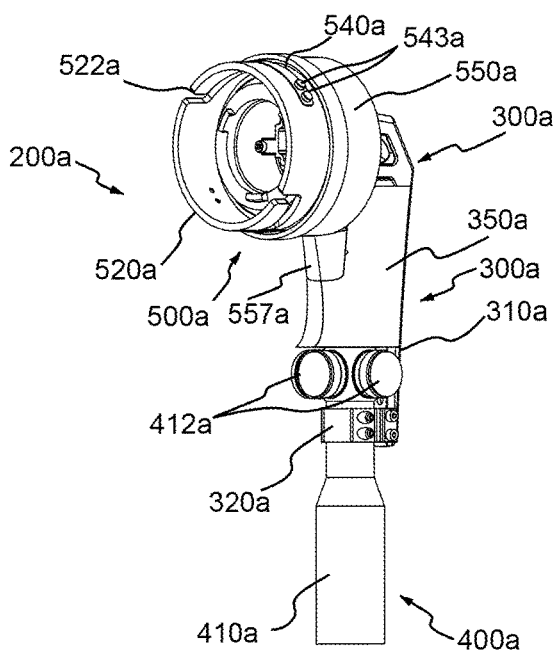

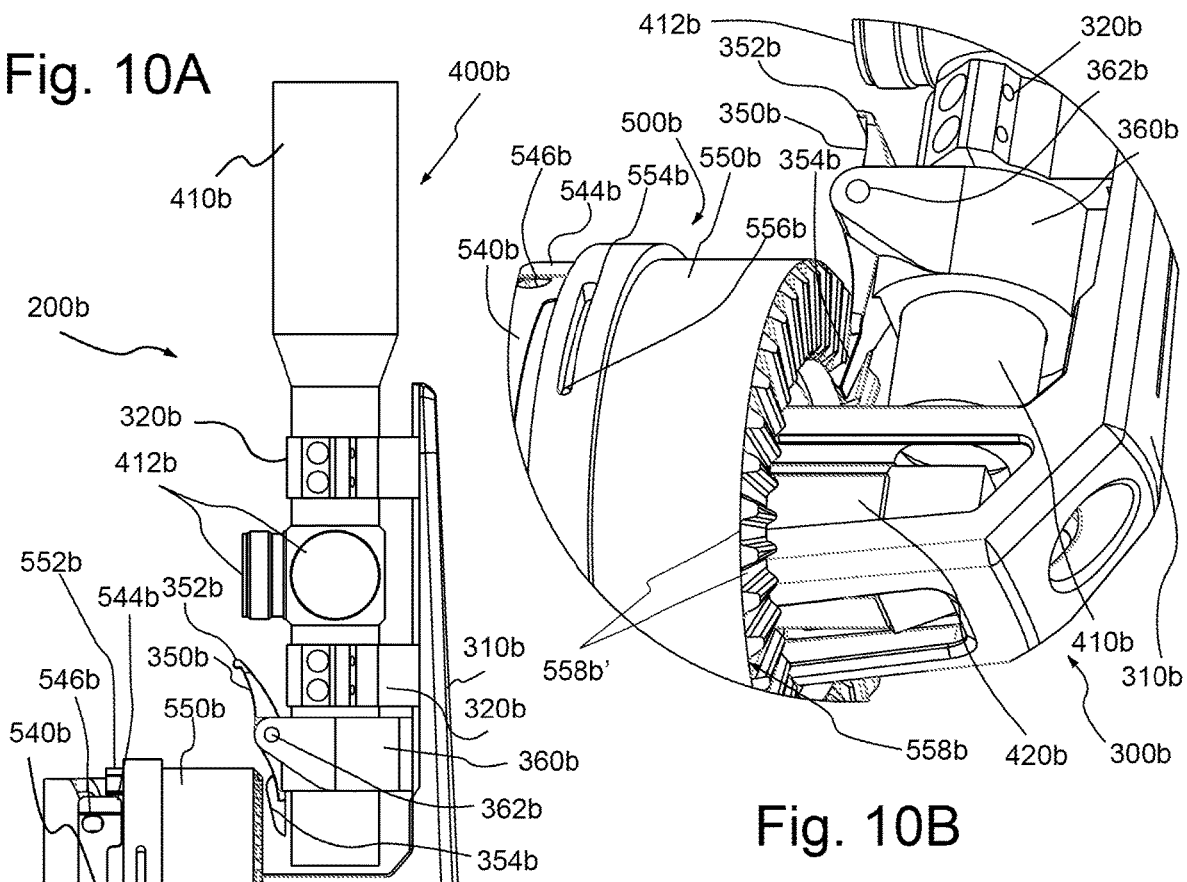
Fig. 10A
Fig. 10B
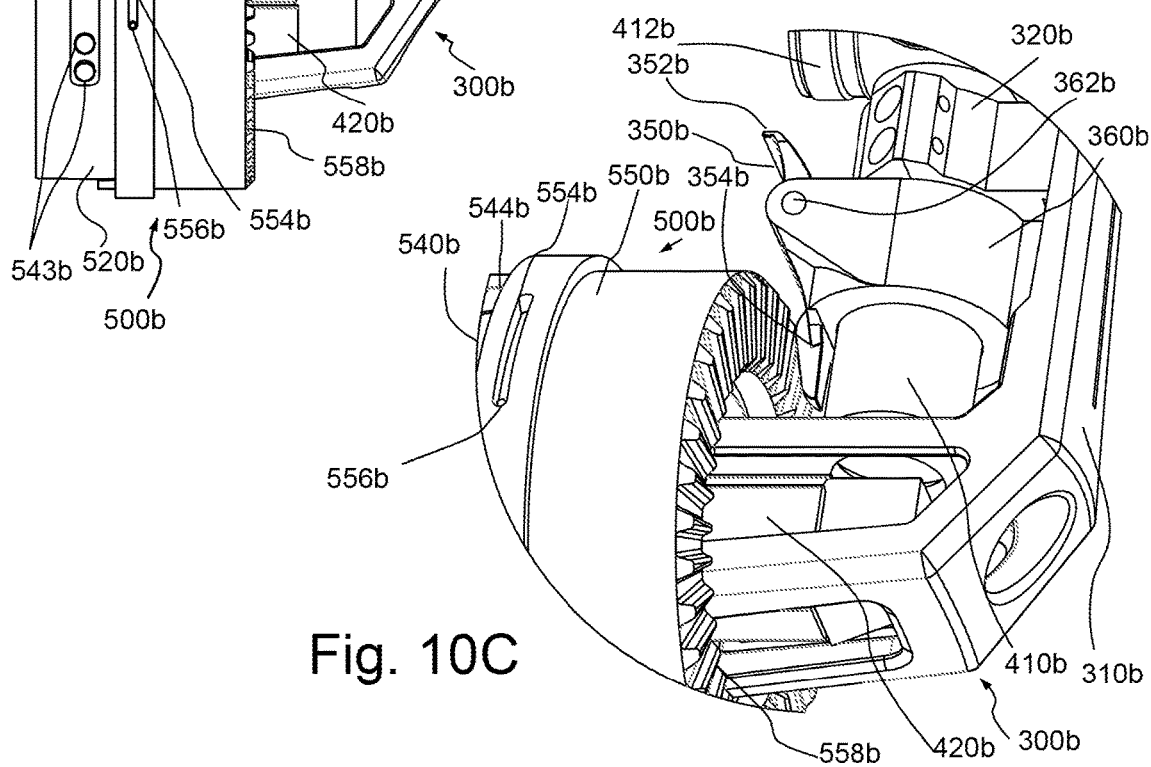
Fig. 10C

ALIGNMENT TOOL FOR OPEN-PATH GAS DETECTORS

BACKGROUND

The following information is provided to assist the reader in understanding technologies disclosed below and the environment M which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Open path gas detection systems include a transmitter and a receiver, typically spaced between 10 and 100 meters apart. However, there are exceptions for both shorter and longer distances. A beam of light, typically infrared light, is emitted from the transmitter, and the receiver calculates the concentration of the gas of interest based on the amount of light absorbed. Because of the optical nature of the system, it is critical that the transmitter and receiver have their respective optical axes aligned with each other with relatively high precision. The best optical path gas detection systems currently available allow for only a total optical axis angular misalignment of less than 1 degree.

To achieve the level of precision required, open path gas detection systems are typically aligned using an optical alignment tool. Because the transmitter and receiver can be located far enough apart that aligning by the naked eye is not possible, alignment tools typically employ some type of scope, similar to a rifle scope. The alignment tool attaches to the housing of each of the transmitter or receiver (whichever end of the system is currently being aligned), utilizing a datum feature to ensure the scopes point of aim is aligned accurately to the device's (transmitter or receiver) optical axis. The scope, which is typically mounted to an arm extending radially from the optical axis of the detector, can have its rotational position adjusted to enable a user to move the scope out of the as of environmental obstacles (for example, walls, poles, etc. in the immediate vicinity) or to bring the scope into a more convenient viewing position.

Additionally, as a verification step that the alignment tool is aligned properly, the radial or rotational position of the scope is typically rotated, for example 180°, while the user looks to see if the scope's point of aim drifts appreciably. Observation of appreciable drift typically requires a return of the alignment tool to the manufacturer for adjustment or repair. Once the alignment tool has been confirmed to be operating correctly, the alignment of the transmitter or receiver is adjusted until the scopes cross hairs are centered directly on the optical window of the housing of the opposite end of the open path system. Then the alignment tool is removed and taken to the opposite end of the open path system and the alignment process is repeated, aiming at the optical window of the previously aligned, first device of the open path system.

The environments in which these open path systems are installed are commonly industrial. Moreover, the open path transmitter and/or receiver are often positioned in difficult to access locations. Many installations require the use of structures or tools (ladders, bucket trucks, scaffolding, etc.) to reach elevated positions to provide access to an open path system, which can make the acts of attaching an alignment tool to and removing an alignment tool from an open path housing difficult and potentially dangerous. Alignment tools currently available either require the use of two hands to attach and secure them to an open path unit or would be extremely awkward to attach and secure with only one hand. Because many of the installation locations for open path units can be in difficult to reach positions, it would be very beneficial for a user to keep one hand on a ladder/scaffolding/bucket truck for balance while attaching and securing an alignment tool. None of the alignment tools currently available are well suited for such scenarios.

SUMMARY

In one aspect, an alignment tool for use in connection with a transmitter or a receiver of an open path gas detection system, wherein each of the transmitter and the receiver includes an interface which includes one or more connectors, includes an optical system having a scope and an attachment system operatively connected to the optical system. The attachment system includes a body including one or more cooperating connectors which cooperate with the one or more connectors of the interface. The body is rotatable about an axis thereof relative to the interface in a first direction to bring the one or more cooperating connectors into connection with the one or more connectors of the interface. The attachment system further includes one or more locking elements which engage the one or more connectors of the interface after a predetermined amount of rotation of the body in the first direction. Engagement of the one or more locking elements with the one or more connectors of the interface forms a state of locked engagement wherein rotation of the body relative to the interface is prevented by the one or more locking elements. A release member is in rotatable connection with the body, wherein rotation of the release member relative to the body in a second direction, opposite the first direction, causes the one or more locking elements to disengage from the one or more connectors of the interface so that the body can be rotated in the second direction to remove the attachment system from connection with the interface.

In a number of embodiments, the alignment tool further includes a scope mounting arm in operative connection to the attachment system to which the scope is attached. The scope mounting arm is rotatable relative to the body of the attachment system when the attachment system is connected to the interface and the one or more locking elements are in engagement with the one or more connectors of the interface. A predetermined level of force may, for example, be required to rotate the scope mounting arm relative to the body of the attachment system. In a number of embodiments, the predetermined level of force is sufficiently high such that the scope mounting aim can be grasped by a user and rotated to bring the attachment system into the state of locked engagement. In a number of embodiments, the alignment tool further includes a locking plate attached to the body such that the locking plate cannot be rotated about the axis of the body relative to the body but can be translated in an axial direction relative to the body, the locking plate being biased into connection with a surface in operative connection with the scope mounting atm.

The one or more connectors of the interface may, tier example, include one or more extending bayonet posts, and the one or more cooperating connectors may include one or more channels formed in the body of the attachment system. In a number of embodiments, the one or more locking elements include one or more spring clips attached to the body. Each of the locking elements may, for example, include a passage therein to engage with one of the one or more extending bayonet posts. In a number of embodiments, the release member includes one or more abutment members which contact and flex the spring clips when the release member is rotated relative to the body in the second direction to disengage the passage of each of the one or more spring clips from the one or more extending bayonet posts. The release member may, for example, be formed as an annulus or ring which extends around a circumference of a section of the body.

In a number of embodiments, the release member is biased into a position in which it does not cause the one or more locking elements to disengage from the one or more connectors of the interface, in a number of embodiments, the alignment tool further includes one or more abutment members which engage the release member after the release member has been rotated in the second direction to disengage the one or more locking elements from the one or more connectors of the interface to prevent the release member from returning into a position in which it does not cause the one or more locking elements to disengage from the one or more connectors of the interface until the body is rotated in the second direction a predetermined distance. The one or more abutment members which engage the release member may, for example, include extending members or pins which are biased into engagement with the release member when the release member has been rotated in the second direction to disengage the one or more locking elements from the one or more connectors of the interface.

In a number of embodiments, the release member includes one or more elements such as contacts, each of which can be placed in cooperative connection with the scope mounting arm to provide rotation of the release member while gripping and rotating the scope mounting arm, and which allow rotation of the scope mounting arm relative to the body when the one or more elements or contacts are not in cooperative connection with the scope mounting arm. The release member may, for example, include an extending flange which is releasably engageable with the scope mounting arm to facilitate rotation of the release member while gripping and rotating the scope mounting arm when the flange is releasably engaged with the scope mounting arm, and which allows rotation of the scope mounting arm relative to the body when the extending flange is disengaged from releasable engagement with the scope mounting arm. In another embodiment, an interlocking member that is controlled b a user is attached to the scope mounting arm. Under control of the user, the interlocking member controllably engages with or disengages from the release member.

In another aspect, a method of aligning at least one of a transmitter and a receiver of an open path gas detection system with the other of the transmitter and the receiver, wherein each of the transmitter and the receiver including an interface including one or more connectors, includes providing an alignment tool. As described above, the alignment tool includes an optical system having a scope and an attachment system operatively connected to the optical system. The attachment system includes a body including one or more cooperating connectors which cooperate with the one or more connectors of the interface. The body is rotatable about an axis thereof relative to the interface in a first direction to bring the one or more cooperating connectors into connection with the one or more connectors of the interface. The attachment system further includes one or more locking elements which engage the one or more connectors of the interface after a predetermined amount of rotation of the body in the first direction. Engagement of the one or more locking elements with the one or more connectors of the interface forms a state of locked engagement wherein rotation of the body relative to the interface is prevented h the one or more locking elements. A release member is in rotatable connection with the body, wherein rotation of the release member relative to the body in a second direction, opposite the first direction, causes the one or more locking elements to disengage from the one or more connectors of the interface so that the body can be rotated in the second direction to remove the attachment system from connection with the interface. The method further includes, attaching the alignment tool to one of the transmitter and the receiver to form the state of locked engagement and using the optical system to align an optical axis of the one of the transmitter and the receiver to which the alignment tool is attached with the optical axis of the other of the transmitter and the receiver.

In a number of embodiments, the alignment tool further includes a scope mounting arm in operative connection to the attachment system to which the scope is attached. The scope mounting arm is rotatable relative to the body of the attachment system when the attachment system is connected to the interface and the one or more locking elements are in engagement with the one or more connectors of the interface. A predetermined level of force may, for example, be required to rotate the scope mounting arm relative to the body of the attachment system. In a number of embodiments, the predetermined level of force is sufficiently high such that the scope mounting arm can be grasped by a user and rotated to bring the attachment system into the state of locked engagement. In a number of embodiments, the alignment tool further includes a locking plate attached to the body such that the locking plate cannot be rotated about the axis of the body relative to the body but can be translated in an axial direction relative to the body, the locking plate being biased into connection with a surface in operative connection with the scope mounting arm.

The one or more connectors of the interface may, for example, include one or more extending bayonet posts and the one or more cooperating connectors include one or more channels formed in the body of the attachment system. In a number of embodiments, the one or more locking elements include one or more spring clips attached to the body. Each of the locking elements may, for example, include a passage therein to engage with one of the one or more extending bayonet posts. In a number of embodiments, the release member includes one or more abutment members which contact and flex the spring clips when the release member is rotated relative to the body in the second direction to disengage the passage of each of the one or more spring clips from the one or more extending bayonet posts. The release member may, for example, be formed as an annulus or ring which extends around a circumference of a section of the body.

In a number of embodiments, the release member is biased into a position in which it does not cause the one or more locking elements to disengage from the one or more connectors of the interface. In a number of embodiments, the alignment tool further includes one or more abutment members which engage the release member after the release member has been rotated in the second direction to disengage the one or more locking elements from the one or more connectors of the interface to prevent the release member from returning into a position in which it does not cause the one or more locking elements to disengage from the one or more connectors of the interface until the body is rotated in the second direction a predetermined distance. The one or more abutment members which engage the release member may, for example, include extending members or pins which are biased into engagement with the release member when the release member has been rotated in the second direction to disengage the one or more locking elements from the one or more connectors of the interface.

As described above, the release member may include one or more elements such as contacts, each of which can be placed in cooperative connection with the scope mounting arm to provide rotation of the release member while gripping and rotating the scope mounting arm, and which allow rotation of the scope mounting arm relative to the body when the one or more contacts are not, in cooperative connection with the scope mounting arm. The release member may, for example, include an extending flange which is releasably engageable with the scope mounting arm to provide rotation of the body while gripping and rotating the scope mounting arm when the flange is releasably engaged with the scope mounting arm, and which allows rotation of the scope mounting arm relative to the body when the extending flange is disengaged from releasable engagement with the scope mounting arm. In another embodiment, an interlocking member that is controlled by a user is attached to the scope mounting arm. Under control of the user, the interlocking member controllably engages with or disengages from the release member.

In a further aspect, an attachment system for use in connection with an interface including one or more connectors includes a body including one or more cooperating connectors which cooperate with the one or more connectors of the interface. The body is rotatable about an axis thereof relative to the interface in a first direction to bring the one or more cooperating connectors into connection with the one or more connectors of the interface. One or more locking elements of the attachment system engage the one or more connectors of the interface after a predetermined amount of rotation of the body in the first direction. Engagement of the one or more locking elements with the one or more connectors of the interface forms a state of locked engagement wherein rotation of the body relative to the interface is prevented by the one or more locking element. A release member is in rotatable connection with the body. Rotation of the release member relative to the body in a second direction, opposite the first direction, causes the one or more locking element to disengage from the one or more connectors of the interface so that the body can be rotated in the second direction to remove the attachment system from connection with the interface.

The present devices, systems, methods and compositions, along with the attributes and attendant advantages thereof, will best be appreciated and understood in view of the following detailed description taken in conjunction with the accompanying drawings.

BRIEF DESCRIPTION OF THE DRAWINGS

FIG. 9A illustrates a front isometric view of another embodiment of an alignment tool hereof wherein a release ring of the alignment tool engages or interlocks with a touch point on the mount of the alignment tool.

FIG. 9B illustrates a front isometric view of the alignment tool of FIG. 9A demonstrating rotation of the mount and scope relative to the attachment system of the alignment tool.

FIG. 9C illustrates another front isometric view of the alignment tool of FIG. 9A demonstrating further rotation of the mount and scope relative to the attachment system of the alignment tool.

FIG. 9D illustrates a front isometric view of the alignment tool of FIG. 9A demonstrating return of the mount and scope to a zero position wherein the release ring of the alignment tool engages or interlocks with the touch point on the mount of the alignment tool so that the user may rotate the entire assembly of the alignment tool for removal.

FIG. 10A illustrates a side view of another embodiment of an alignment tool hereof wherein a release ring of the alignment tool engages or interlocks with the mount of the alignment tool under control of the user.

FIG. 10B illustrates an enlarged isometric view of a portion of the alignment tool of FIG. 10A in which a trigger or interlocking member attached to the mount, which interacts with a grooved rearward surface of the release ring, is engaged with the grooves surface of the re lease ring.

FIG. 10C illustrates another enlarged isometric view of the alignment tool of FIG. 10A in which the interface member of the trigger or interlocking member is disengaged from the grooves surface of the release ring.

DETAILED DESCRIPTION

It will be readily understood that the components of the embodiments, as generally described and illustrated in the figures herein, may be arranged and designed m a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art, will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a biasing member" includes a plurality of such biasing member and equivalents thereof known to those skilled in the an, and so forth, and reference to "the biasing member" is a reference to one or more such biasing members and equivalents thereof known to those skilled in the an and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

Figure 1:
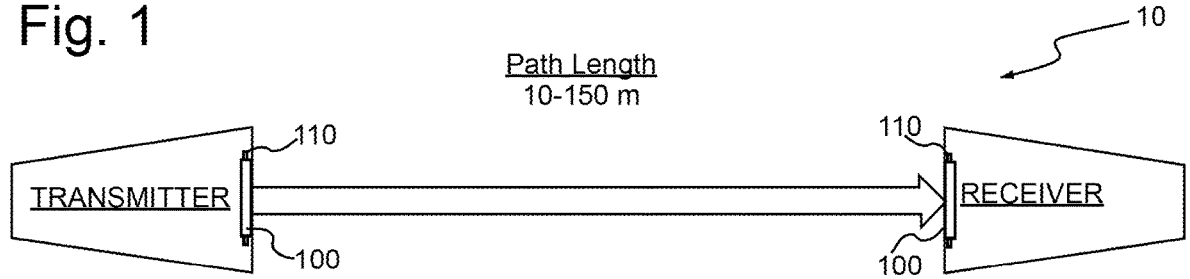
FIG. 1 illustrates schematically an embodiment of an open path gas detector system hereof including a transmitter and a receiver with representative distances therebetween.

In a number of embodiments, an alignment tool hereof, which includes an attachment system for attachment or connection to open path gas detection unit and an optic system for ensuring alignment of such units, can be held, attached, and removed safely from the open path gas detection unit (that is, a transmitter or receiver as illustrated in FIG. 1A) with one hand. Alignment tools 200 (see, for example, FIGS. 3A through 7B) hereof may, for example, be thrilled as an assembly including a base or mount 300, to which an optics system 400, including a scope 410, a mirror or prism 420, and a mirror/prism holder 430, and an attachment system 500 are operatively attached. Scope 410, which is similar to scopes used in connection with rifles, is attached to a scope mounting arm 310 of mount 300 via brackets or scope rings 320. Scope 410 may include manufacturer-set adjustment mechanisms or adjustors 412 as described above to, for example, adjust the crosshairs of be scope.

Figure 6A:
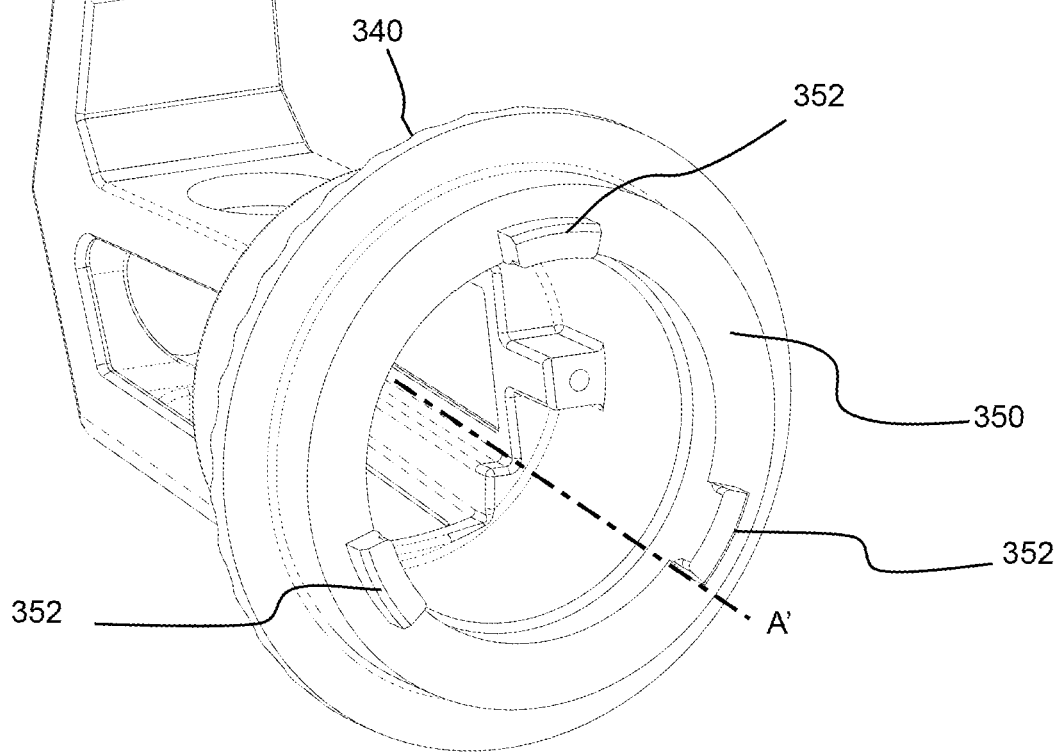
FIG. 6A illustrates a rear, isometric view of a mount of the alignment tool of FIG. 3A.
Figure 6B:
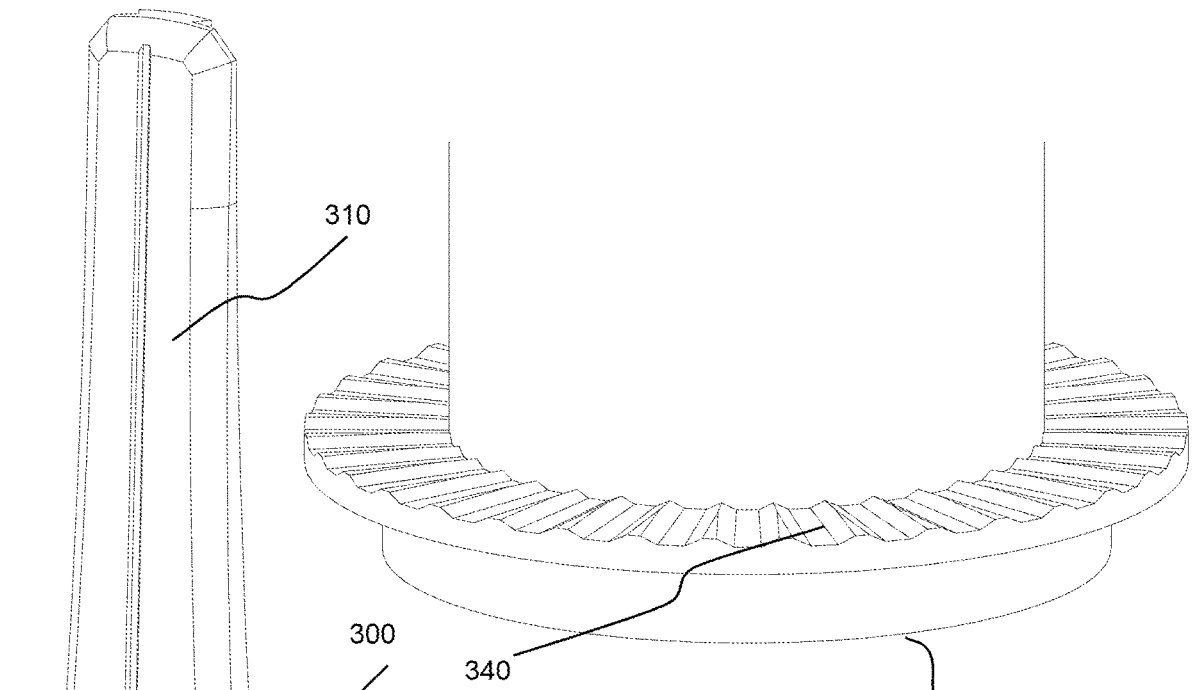
FIG. 6B illustrates a front, isometric view of a portion of the mount of the alignment tool.
Figure 6C:
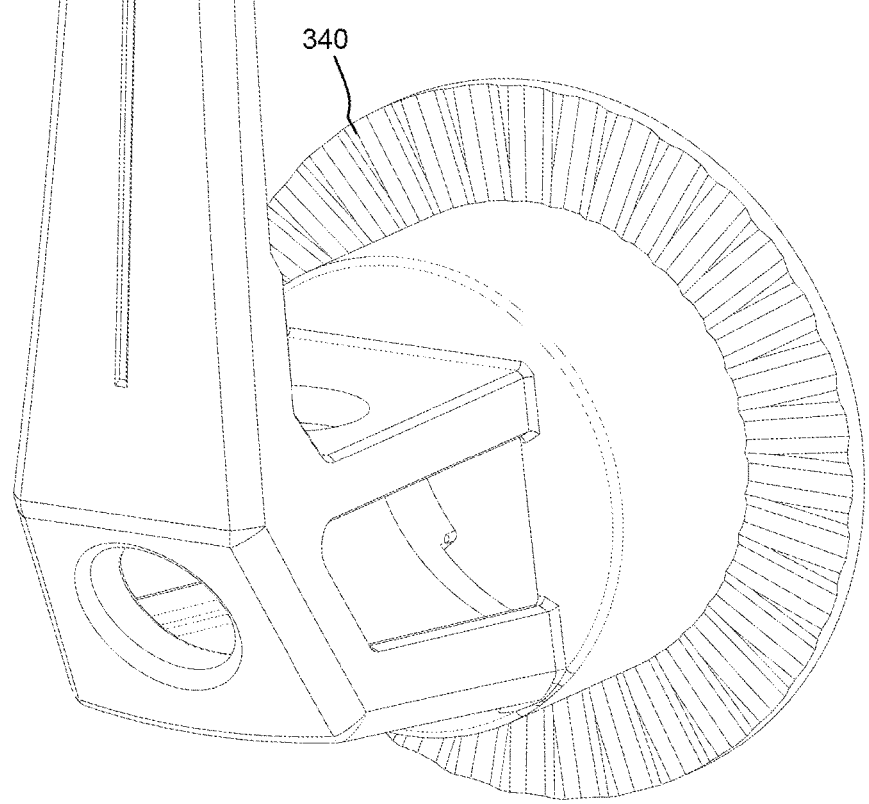
FIG. 6C illustrates a front, isometric view of the mount of the alignment tool including a grooved surface.

Referring, for example, to FIGS. 34 and 6A, in the illustrated embodiment a first portion of mount 300 is formed around (although not necessarily symmetrically around) an axis A'. Attachment system 500 is operatively connected to the first portion of mount 300. A second portion of mount 300, which includes scope mounting arm 310, extends at an angle away from axis A' in, for example, a perpendicular or radial direction.

In a number of embodiments, alignment tools hereof employs a bayonet-style attachment system 500 to attach to an attachment point or interface 100 (see, FIG. 2) of the transmitter or receiver upon alignment of axis A' with axis A of interface 100 and engagement of attachment system 509 with interface 100 as described below. In the illustrated embodiment, interface 100 includes one or more bayonet posts or pins 110 extending radially therefrom (two in the illustrated embodiment) which cooperate with attachment system 500 of alignment tool 200 via mounting slots or channels 522 of a body 520 thereof as, for example, illustrated in FIGS. 3A through 3D, 4A and 4B.

Figure 2:
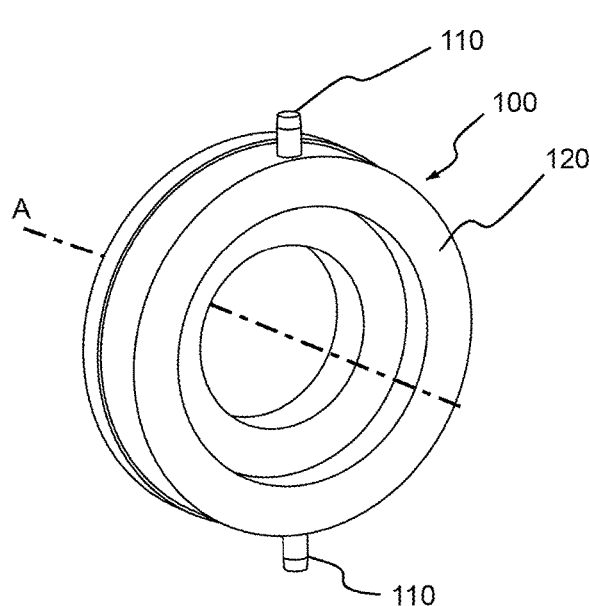
FIG. 2 illustrates an embodiment of an attachment point or interface hereof.

Various bayonet-style attachment mechanisms do not have a mechanism or system for adequately locking in place once connected to a bayonet connection interface as, for example, illustrated in FIG. 2. Such bayonet-style attachment mechanisms may simply rely on friction to stay secured. Without a locking mechanism or system, as the user adjusts the position of a scope of an alignment tool, the user may inadvertently remove the alignment tool/scope assembly from the interface. This possibility can make adjusting the scope difficult and unsafe. Moreover, the alignment tool is subject to accidentally coming loose if the user bumps into the mechanism or tries to adjust the position of the scope with a single hand without using their other hand to ensure the alignment tool remains secured to the housing interface of the transmitter or receiver. Accidentally dismounting the alignment tool can result in the alignment tool falling and getting damaged. As set forth above, transmitter and receiver may be positioned at significant height. Accidentally dismounting the alignment tool is also dangerous as a falling alignment tool could hit something or someone.

To address such problems, attachment system 500 of alignment tool 200 hereof includes a locking mechanism including, for example, one or more locking elements such as spring clips 540 to secure the alignment tool 200 to the housing of the transmitter or receiver of an open path system via attachment point or interface 100 thereof. The locking mechanism locks attachment system 500 of alignment tool 200 in place and prevents accidental loosening or detachment from occurring as a result of bumping alignment tool 200 or repositioning the scope. In a number of representative embodiments, to remove the alignment tool 200 from connection with interface 100, a release member or element (a release ring 550 in the illustrated embodiment; see FIGS. 3A through 4B and) is moved (for example, rotated) relative to body 520 to disengage the locking elements (for example, lift spring clips 540 in the illustrated embodiment). In the illustrated embodiment, release ring 550 causes movement or flexing of spring clips 540 a sufficient radial distance to clear the features (for example, posts 110 of attachment point or interface 100) to which they were engaged during attachment, thereby allowing for the free rotation of attachment system 500 and enabling alignment tool 200 to be detached.

With release ring 550 rotated to the "unlocked" position, attachment system 500 operates similarly to bayonet-style attachment mechanisms without locking mechanisms and it's possible that a user may forget to place release ring 550 back to the "locking" position. To eliminate this risk, a biasing element such as a spring 560 (see, FIGS. 3D and 3F) such as a torsion spring may be provided to return release ring 550 to the "locking" position automatically as soon as the user lets go of release ring 550. It is also possible to implement a secondary locking mechanism attached to alignment tool 200 which holds release ring 550 in the "unlocked" position until alignment tool 200 is physically removed from open path gas detector housing interface 100. Upon such removal, the secondary locking mechanism would release and allow spring 560 to return release ring 500 to the "locking" position such that locking occurs automatically when alignment tool 200 is once again placed in connection with a housing interface 100. In the illustrated embodiment, spring 560 includes hook-shaped attachment elements 562 which attach to an axially extending attachment member or post 529 (see, for example, FIG. 3F) on body 520 and to an axially extending attachment member, post, or flange 559 on release ring 550 (see, for example, FIG. 5D).

Alignment tool 200 is configured to interface with a structure, referred to as the attachment point or interface 100, that has a front datum surface or face 120 and, in the illustrated embodiment, two posts 110 oriented radially outward relative to an axis A as illustrated in FIG. 2. Thus, in the illustrated embodiment, body 520 of attachment system 500 includes two bayonet channels 522 that are shaped such that as body 520 rotates and bayonet posts 110 move along channels 522, the angle or curve of channels 522 cause posts 110 to pull body 520 toward interface 100. The resulting linear action will eventually bring an alignment datum face 350 of alignment tool 200 into contact with datum face 120 of interface 100. Datum features 352 control the perpendicular distance between the A' axis and optical axis A of the transmitter or receiver. In other words, data features 352 operate to keep axis A' centered relative to interface 100. To reduce the total number of parts or components in alignment tool 200 in the illustrated embodiment, alignment datum face 350 was combined into or formed integrally with mount 300 as a single part (see, for example, FIG. 6A), which is referred to herein as mount 300 (see, for example, FIGS. 6A through 6C).

In a number of embodiments, contact between datum face 120 and alignment datum face 350 occurs before posts 110 have reached the ends of channels 522. Therefore, as body 520 continues to translate along its cylindrical axis A', mount 300 will put pressure on a locking plate 600 (see FIGS. 3D, 7A and 7B), which in turn will apply pressure to a biasing element such as a wave spring 650, causing wave spring 650 to compress. As clear to one skilled in the art, other biasing members such as helical compression springs or tension springs may be used in place of the wave springs or torsion springs, respectively. Representative examples of biasing members or elements include resilient members or elements such as springs elements, elastomeric elements, etc. Biasing member/spring 650 maintains alignment datum face 350 flush against interface datum face 120. By keeping such datum faces flush against each other and through the operation of datum features 352, axes A and A' are maintained parallel.

Figure 7A:
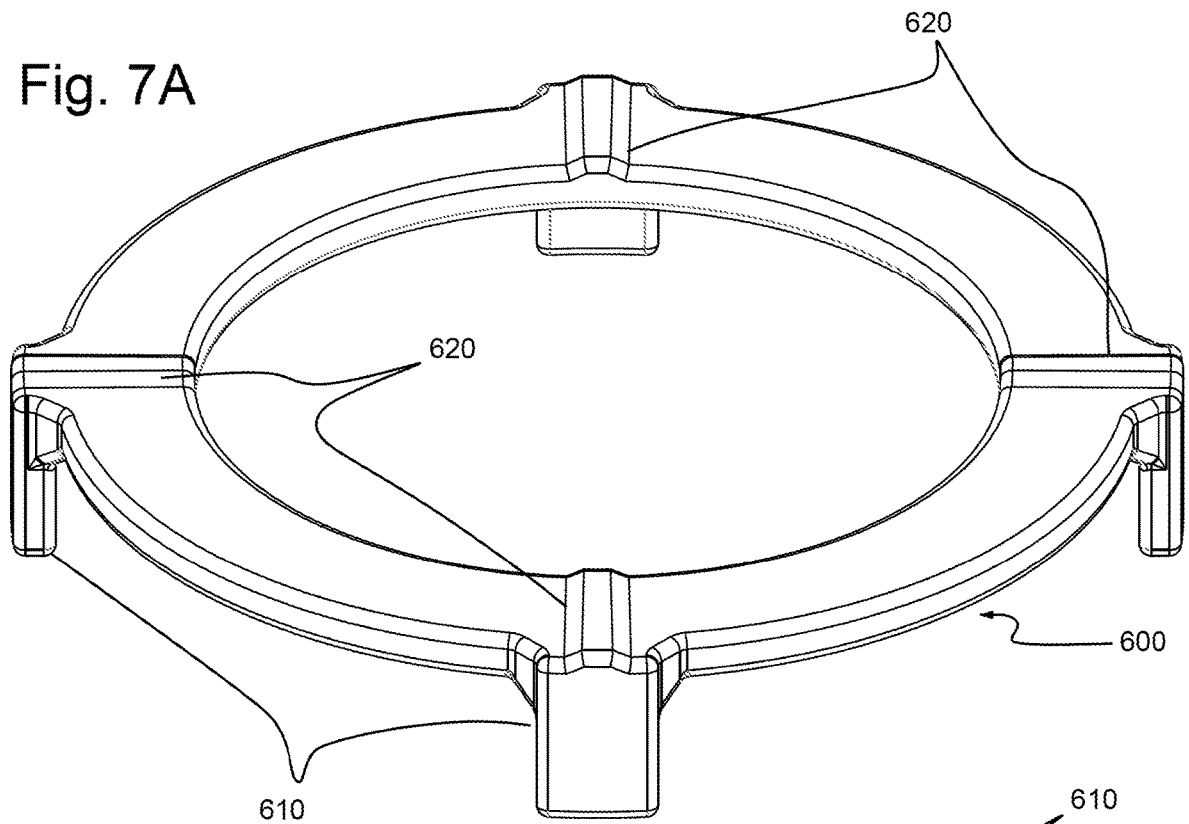
FIG. 7A illustrates a rear, isometric view of a locking ring of the alignment tool of FIG. 3A.
Figure 7B:
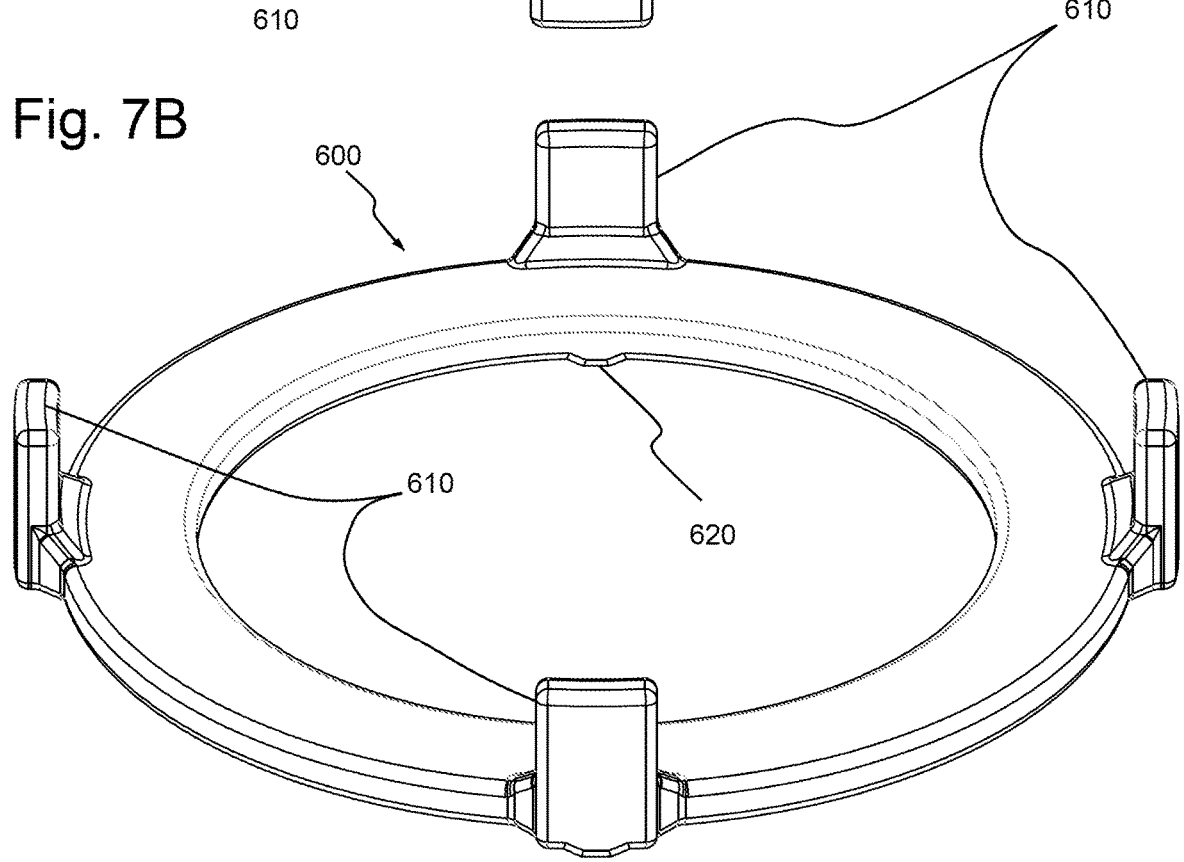
FIG. 7B illustrates a front, isometric view of the locking ring.

As illustrated in FIGS. 7A and 7B, locking plate 600 includes a plurality of axially extending legs 610 that cooperate with notches 524 (see FIG. 5B) of body 520 to prevent locking plate 600 from rotating relative to body 520 (about axis A') while simultaneously providing support to promote sliding or translating of locking plate 600 linearly along axis A' within body 520. Additionally, locking plate 600 includes a plurality of extending members or ribs 620 that engage with a corresponding set of grooves 340 formed on mount 300. The sides of ribs 620 and grooves 340 are angled or curved to allow the mount 300 (and thus scope 410) to rotate about axis A' relative to locking plate 600 (and body 520) when sufficient rotational force is applied. The ease with which mount 300 can rotate relative to locking plate 600 is dependent on the angle of the faces and the normal force between them (that is, the amount of force being exerted by wave spring 650).

By setting the angle of the ribs and grooves such that the force required for relative rotation of locking plate 600/attachment system 500 to mount 300 is greater than the force required to compress wave spring 650, scope mounting arm 310 of mount 300 is the only portion of alignment tool 200 that a user would need to be holding when the user installs alignment tool 200 on attachment point or interface 100. Using ergonomics, anthropometrics, and human factors to drive the design of alignment tools hereof, the scope mounting arm area becomes a comfortable and intuitive location to hold the alignment tool while providing the proper leverage to easily manipulate the attachment system to effect attachment to interface 100.

Figure 3A:
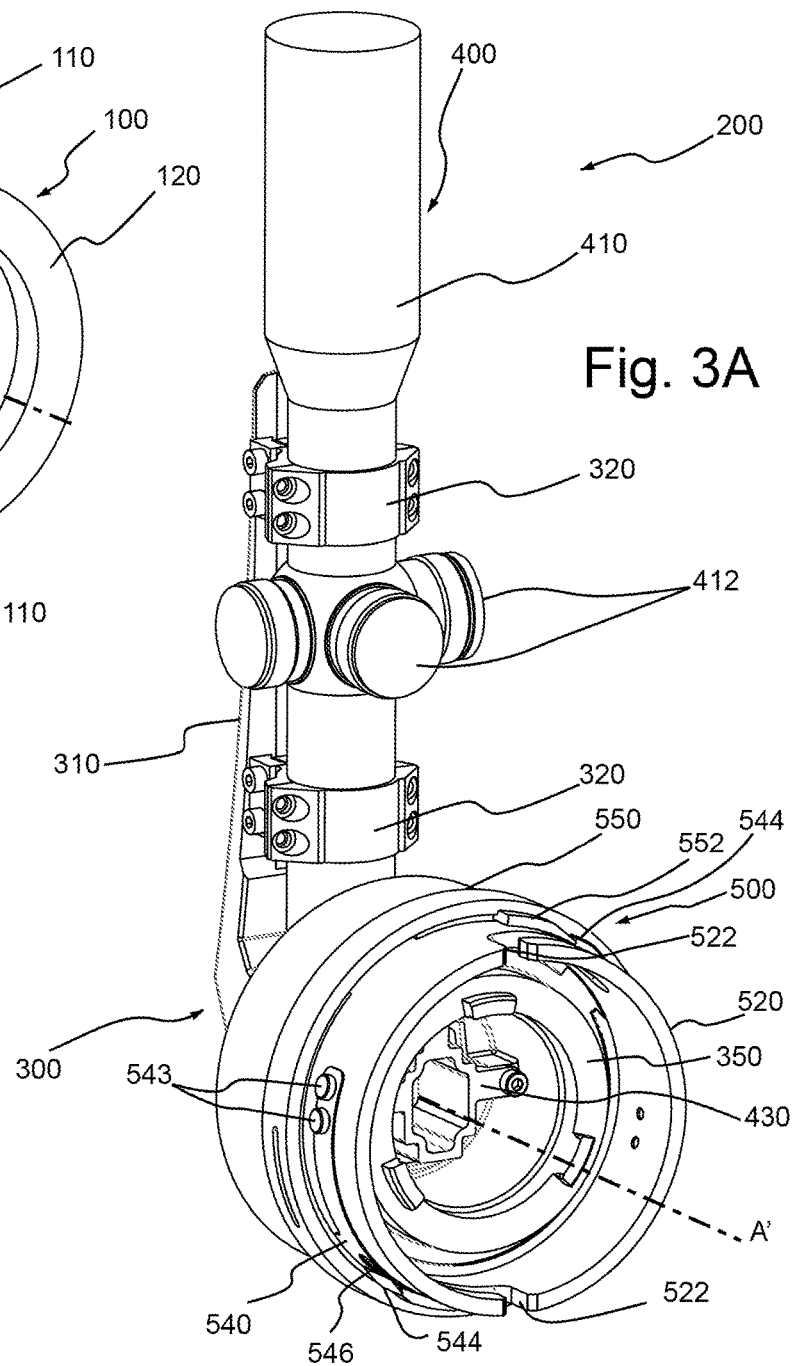
FIG. 3A illustrates a rear isometric view of an embodiment of an alignment tool hereof.
Figure 3B:
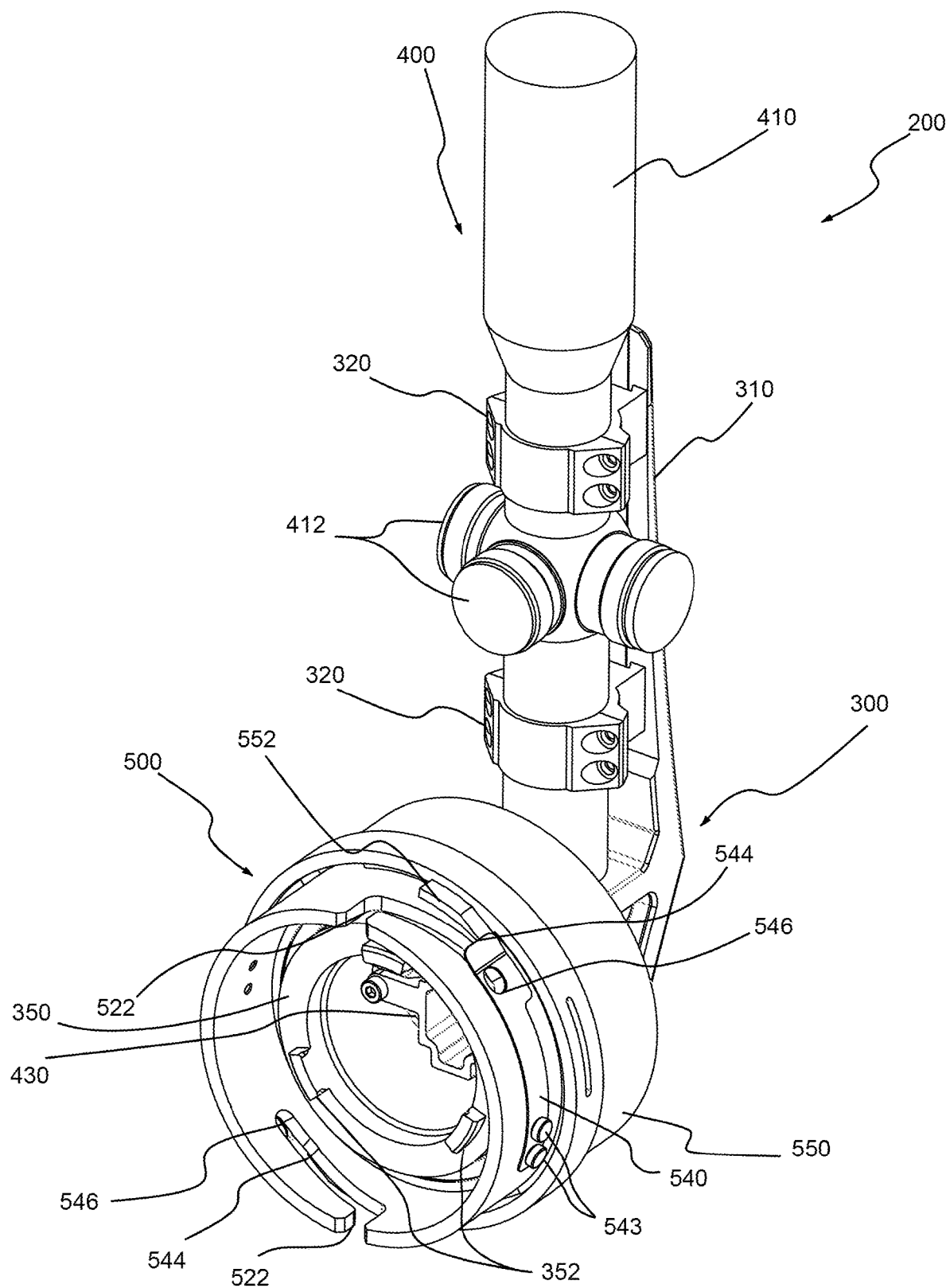
FIG. 3B illustrates another rear isometric view of the alignment tool of FIG. 3A.
Figure 3C:
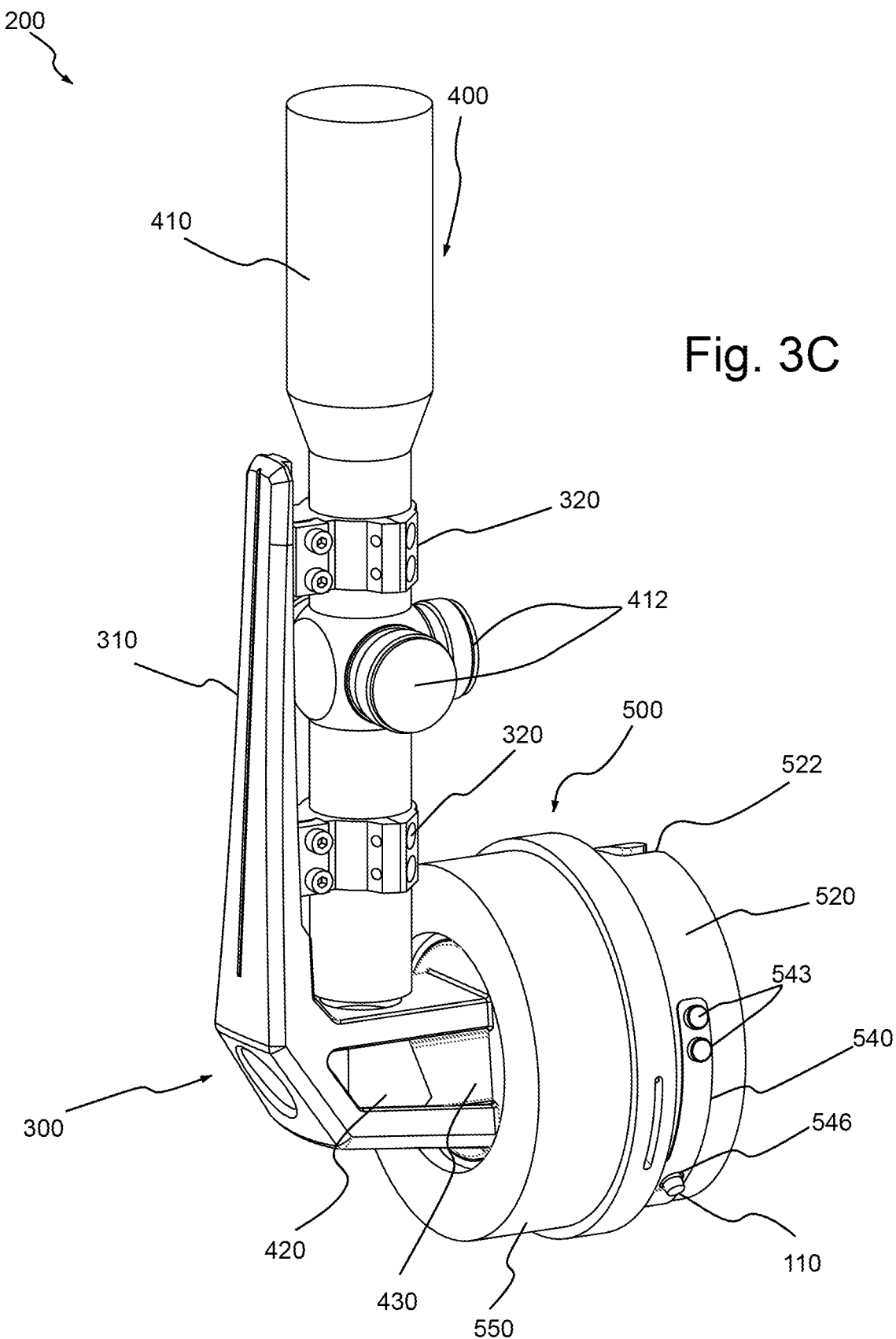
FIG. 3C illustrates a front isometric view of the alignment tool of FIG. 3A wherein the alignment tool is in locked engagement with the interface of FIG. 2.
Figure 3D:
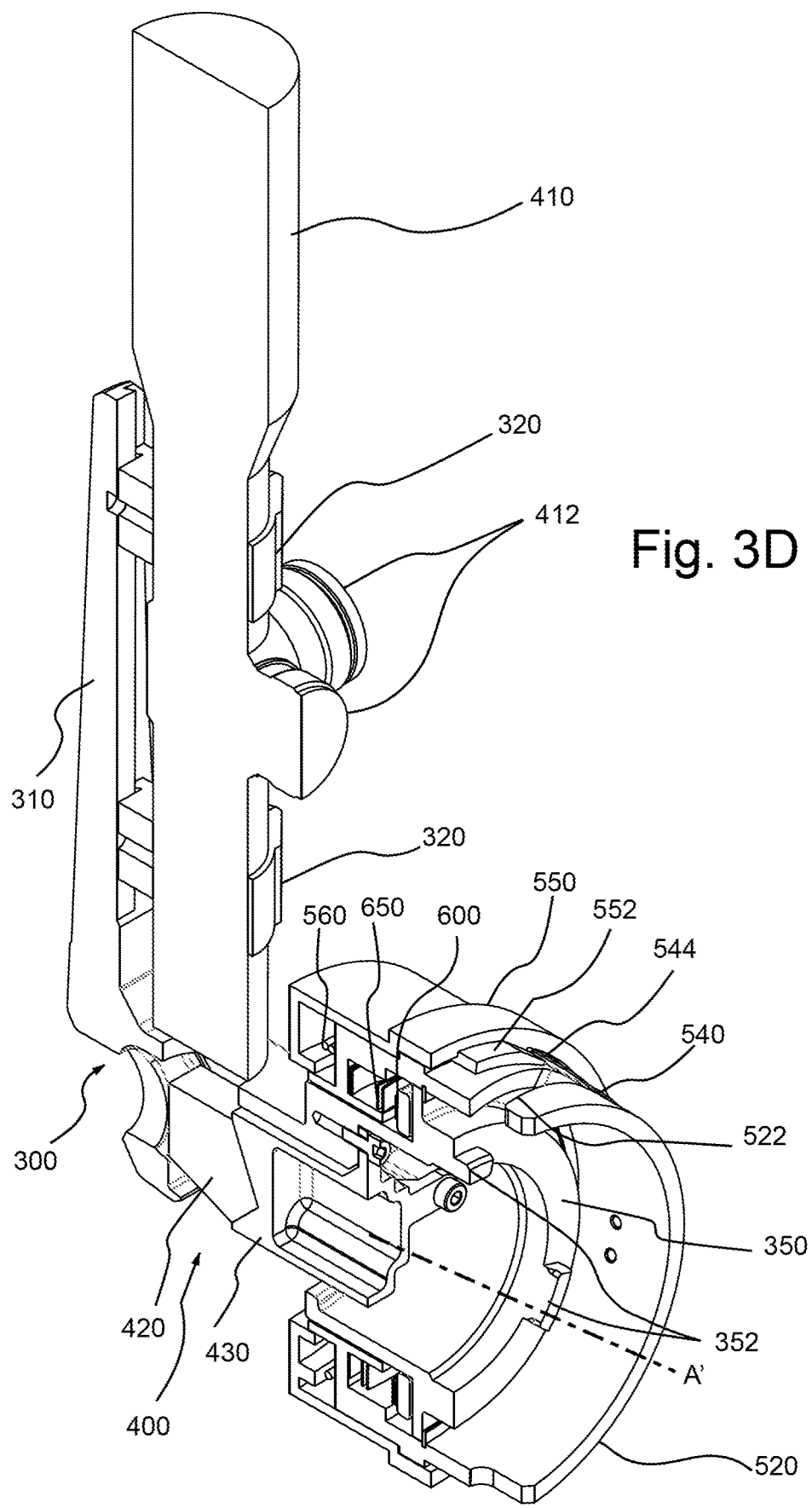
FIG. 3D illustrates a rear, cutaway isometric view of the alignment tool of FIG. 3A.
Figure 3E:
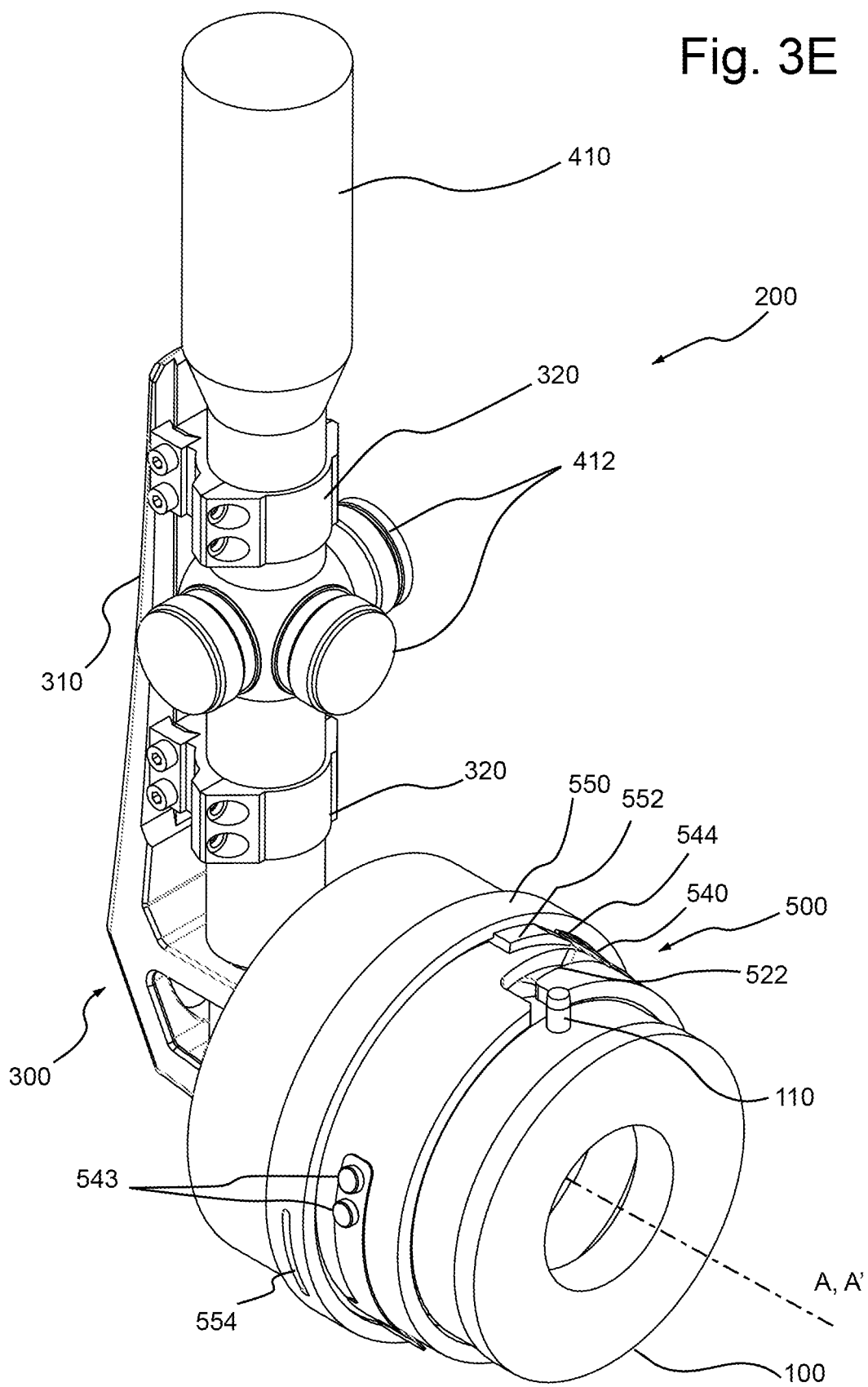
FIG. 3E illustrates a rear isometric view of the alignment tool of FIG. 3A aligned for connection with the interface of FIG. 2.
Figure 3F:
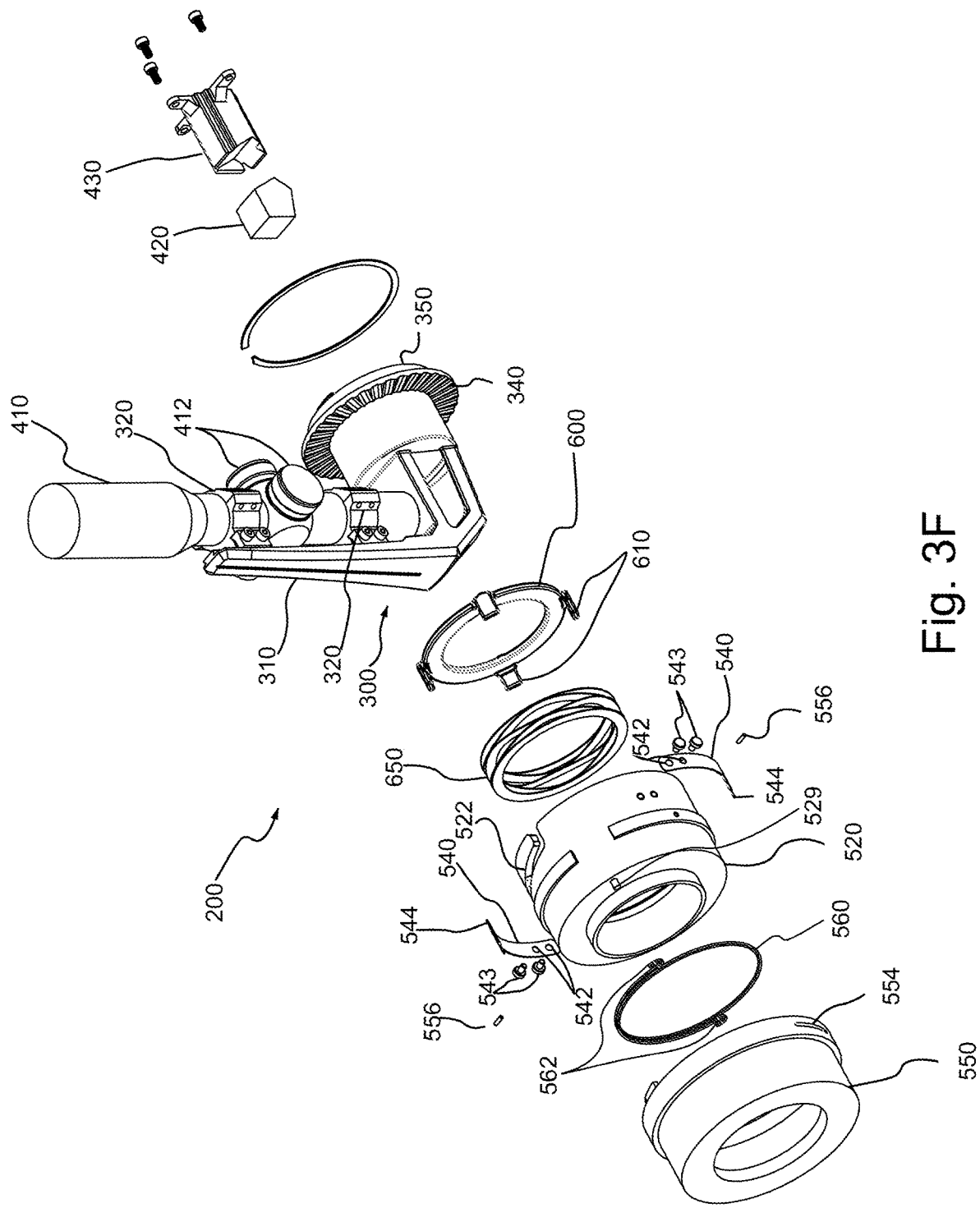
FIG. 3F illustrates an isometric, exploded view of the alignment of FIG. 3A.
Figure 4A:
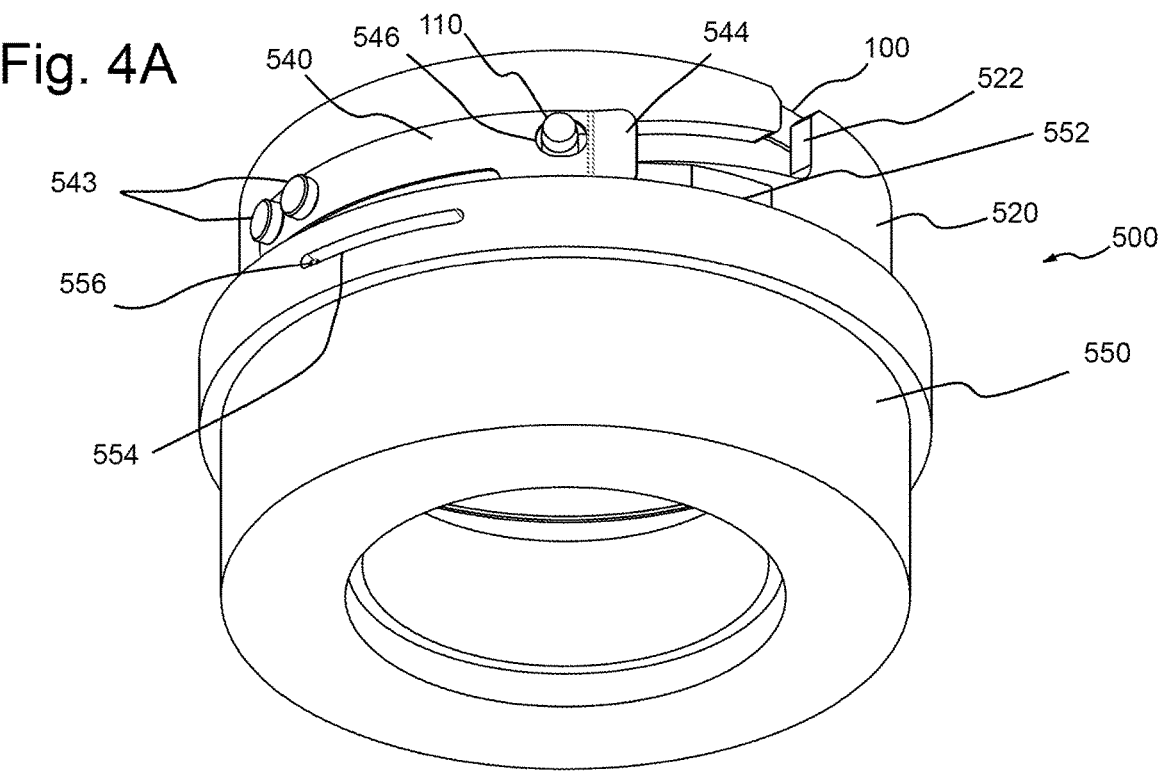
FIG. 4A illustrates an isometric view of the attachment system of the alignment tool of FIG. 3A wherein locking elements including spring dips are engaged with connectors of the interface of FIG. 2 which includes extending bayonet posts.

During such attachment, once body 520 has rotated a defined distance, bayonet posts 110 will contact or engage spring clips 540, which are attached to body 520 via connectors 543 (for example, bolts) which extend through passages 542 in spring clips 540 (see, for example, FIG. 3F). Spring clips 540 may, for example, including a leading edge 544 which is angled away from an exterior surface of body 520 when attached thereto, which facilitates spring clips 540 to ride up and over bayonet posts 110 upon contact therewith and flexing thereby. A passage 546 in spring clips 540 then allows spring clips 540 to spring down over posts 110 to a relaxed state as illustrated in FIG. 4A, thereby locking attachment system 500 in place.

In that regard, with passages 546 of spring clips 540 around posts 110, body 520 and locking plate 600 can no longer rotate about axis A'. This locking enables the user to exert sufficient force upon scope mounting arm 310 of mount 300 to exert a level of pressure on locking plate 600 via grooves 340 with ribs or ridges 620 to overcome the wave spring force, which forces locking plate 600 away from the surface of mount 300 in which grooves 340 are formed and eventually driving ridges 620 on locking plate 600 out of grooves 340 on mount 300. Mount 300 can then rotate a set number of degrees until ribs 620 on locking plate 600 fall into the next set grooves 340 on mount 300. In this manner, mount 300, including scope mounting arm 310, can fully rotate about axis A' of body 520, allowing the user to adjust the rotational position of scope 410.

Figure 4B:
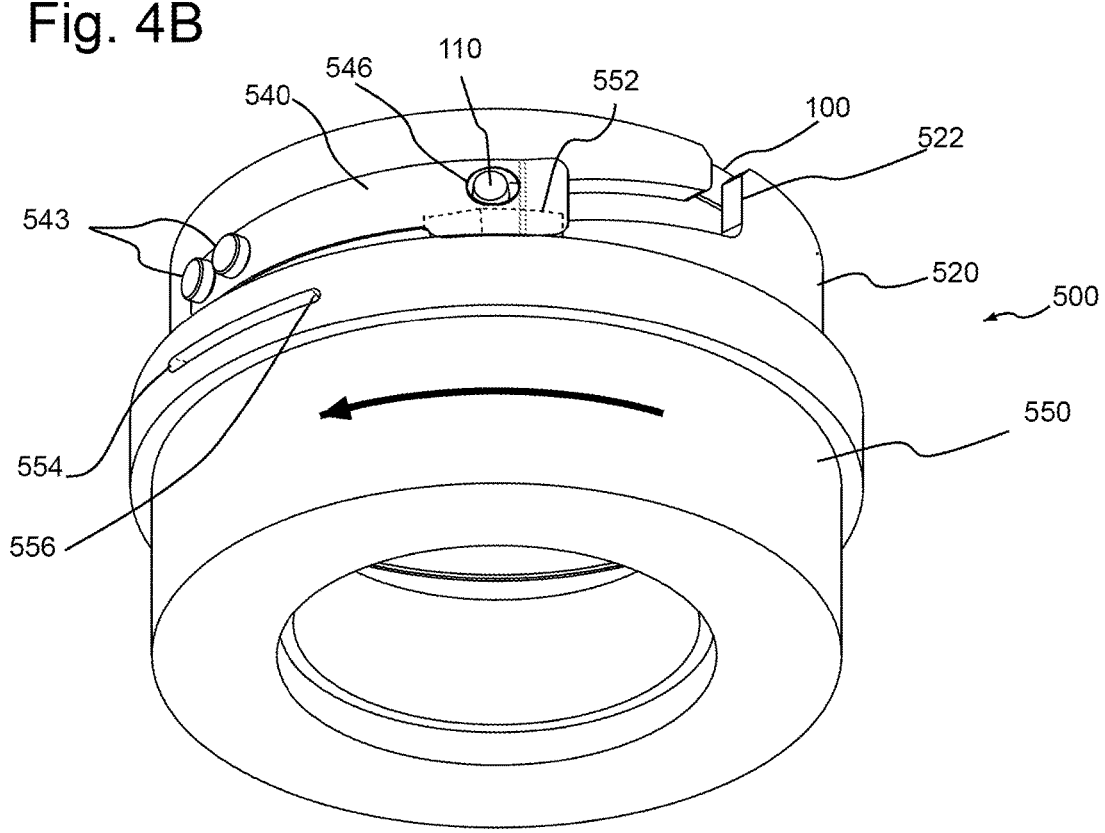
FIG. 4B illustrates another isometric view of the attachment system wherein a release member of the attachment system has been rotated relative to a body of the attachment system to cause disengagement of the locking element from the connectors of the interface of FIG. 2.
Figure 5A:
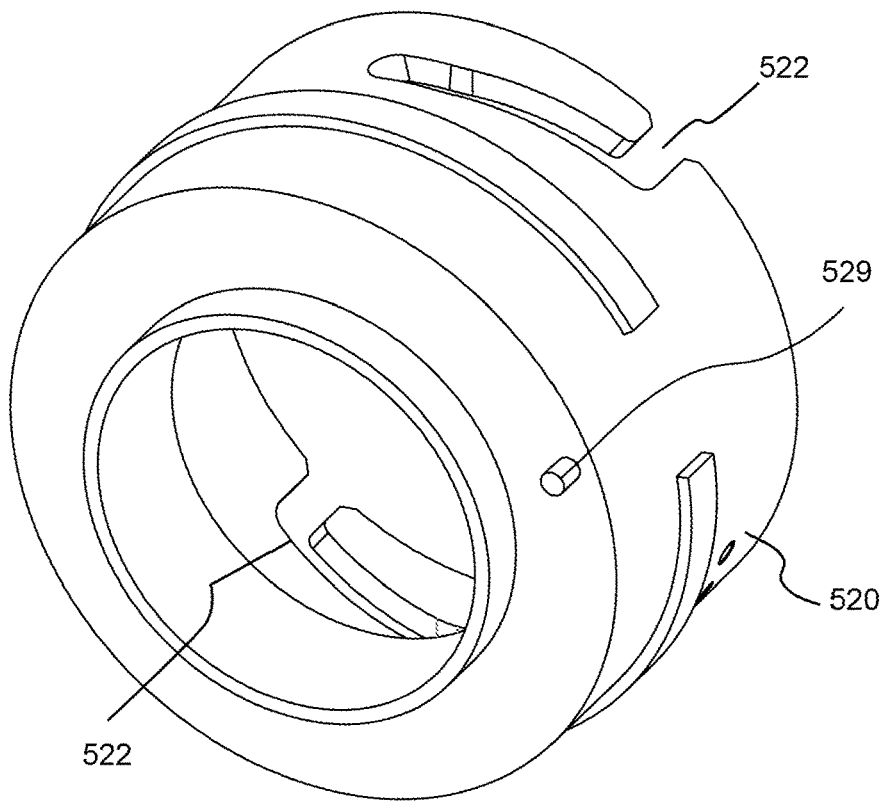
FIG. 5A illustrates an isometric view of the body of the attachment system.
Figure 5B:
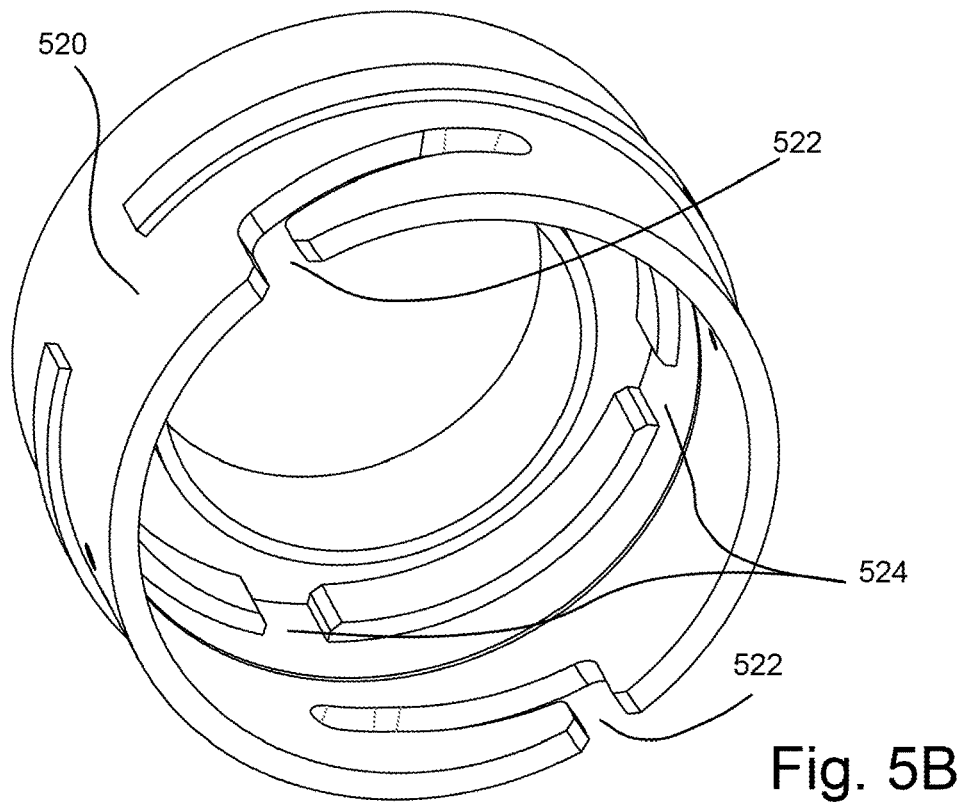
FIG. 5B illustrates another isometric view of the body of the attachment system.
Figure 5C:
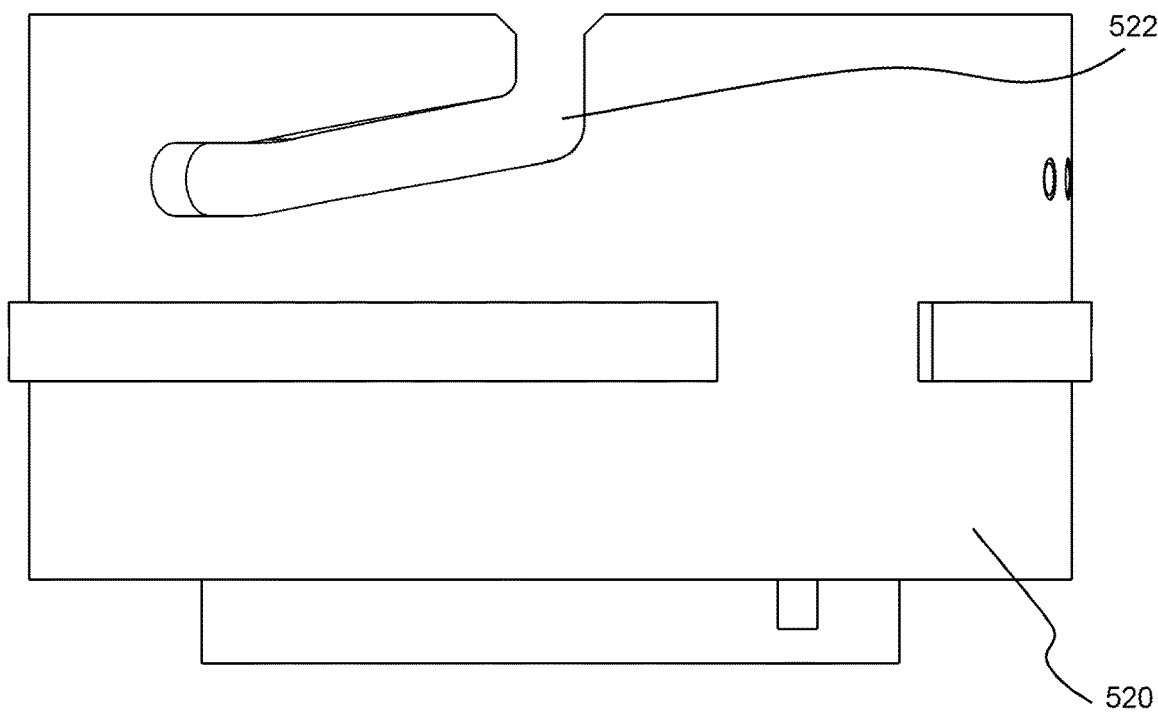
FIG. 5C illustrates a side view of the body of the attachment system.
Figure 5D:
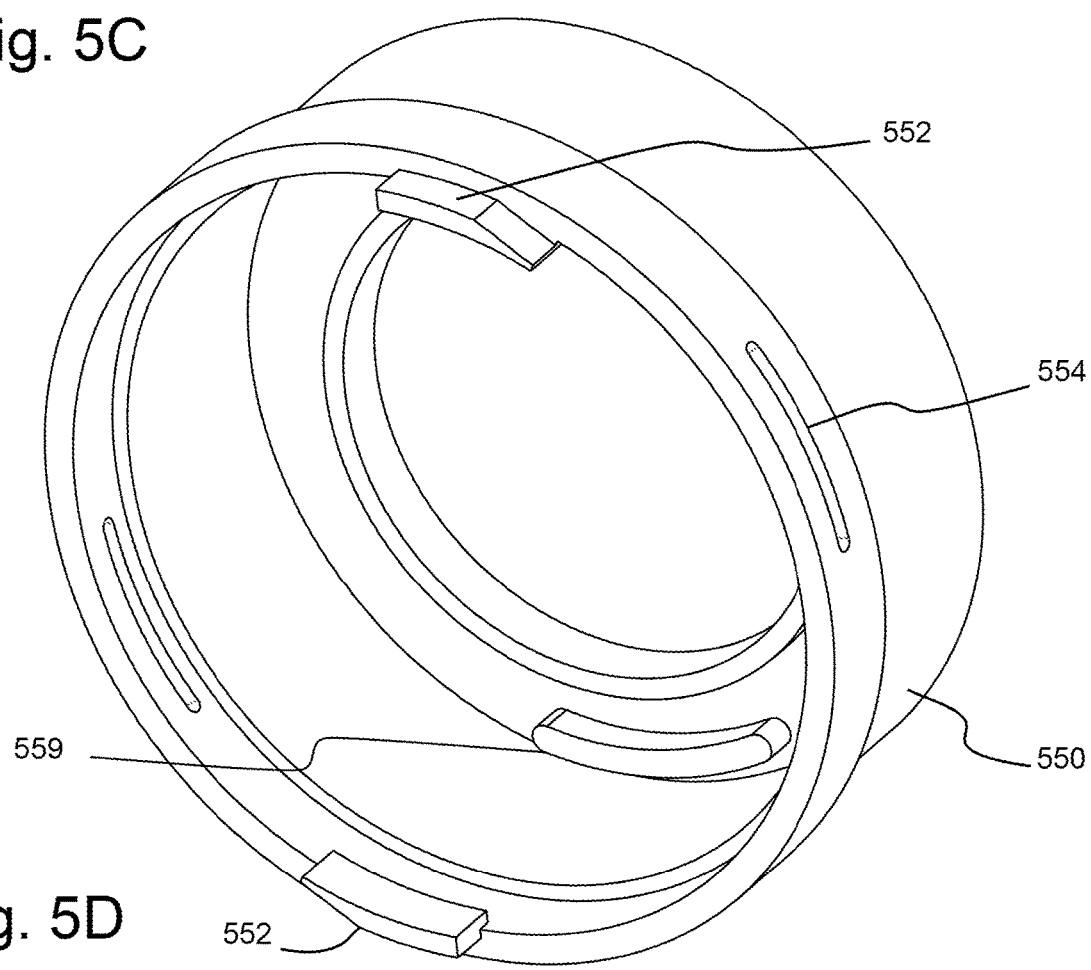
FIG. 5D illustrates an isometric view of the release member of the attachment system.

To remove alignment tool 200 from attachment point or interface 100, release ring 550 is rotated in the direction opposite (see arrow in FIG. 4B) to the direction that alignment tool 200 was rotated in installation. For example, if alignment tool 200 was rotated clockwise to install on attachment point or interface 100, then release ring 550 would be rotated counterclockwise to remove alignment tool 200 from attachment point or interface 100. The release ring may, for example, include ramped abutment members 552, one for each spring clip 540, that will slide under each spring clip 540 and flex/lift spring clips 540 over bayonet posts 110 as illustrated in FIG. 4B. At this point, attachment system 500 is no longer locked in place relative to interface 100. Therefore, continuing to rotate release ring 550 will rotate body 520 as well. Because the rotational direction of release ring 550 is opposite to the rotational direction in which attachment system 500 was initially secured to interface 100, the entire assembly of alignment tool 200 can be removed from attachment point or interface 100 in one fluid motion using a single hand, all driven by release ring 550. Release ring 550 includes slots 554 in which a set screw 556 rides. The cooperation of set screws 556 and slots 554 serves as a stop to limit the range of rotation of the release ring 550 and transfers the rotation force from the release ring 550 to the entire alignment tool 200 during removal as described above (see FIGS. 4A and 4B).

Once removed from attachment point or interface 100 and the user lets go of release ring 550, a torsion spring 560 will reset release ring 550 back to its initial position. This, in turn, will remove abutment member 552 from contact with spring clips 540 and allow spring clips 540 to relax or lower down to their initial, unflexed positions. At this point, alignment tool 200 is in the same state as it was prior to installation and is ready to be secured to another attachment point/interface 100.

Figure 8A:
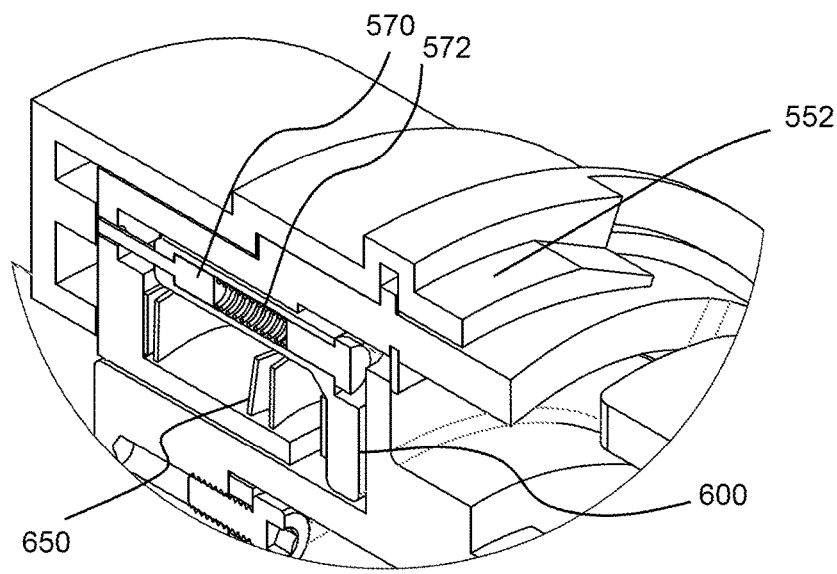
FIG. 8A illustrates an isometric view of a portion of an embodiment of an attachment system of an alignment tool hereof including an embodiment of a locking pin wherein the components of the attachment system are in an unattached or natural state before attachment to an interface.
Figure 8B:
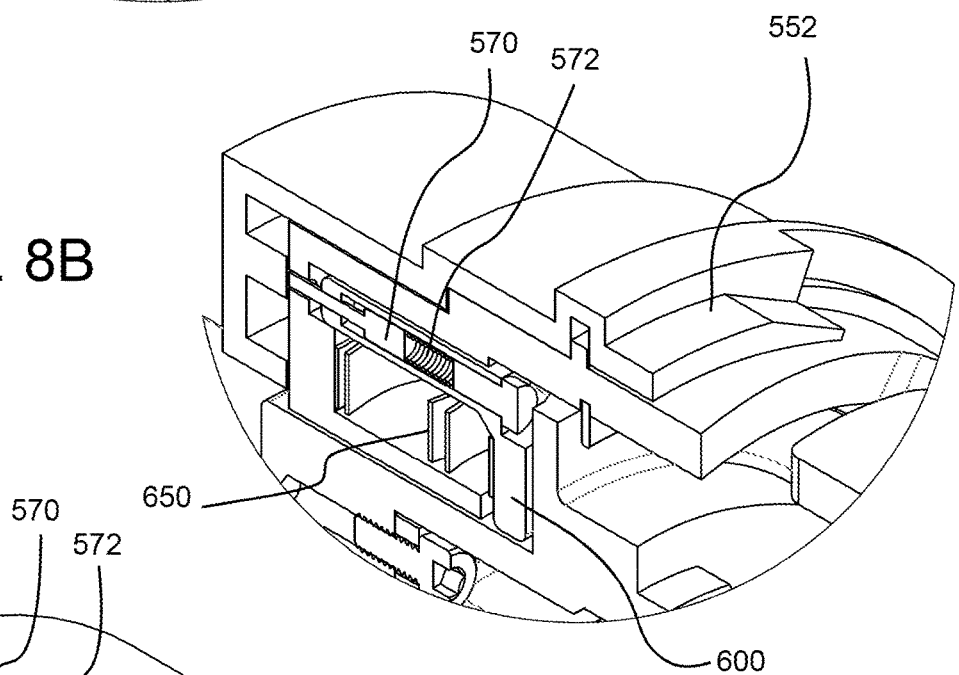
FIG. 8B illustrates an isometric view of the portion of the attachment system of FIG. 8A attached to an interface (not shown).
Figure 8C:
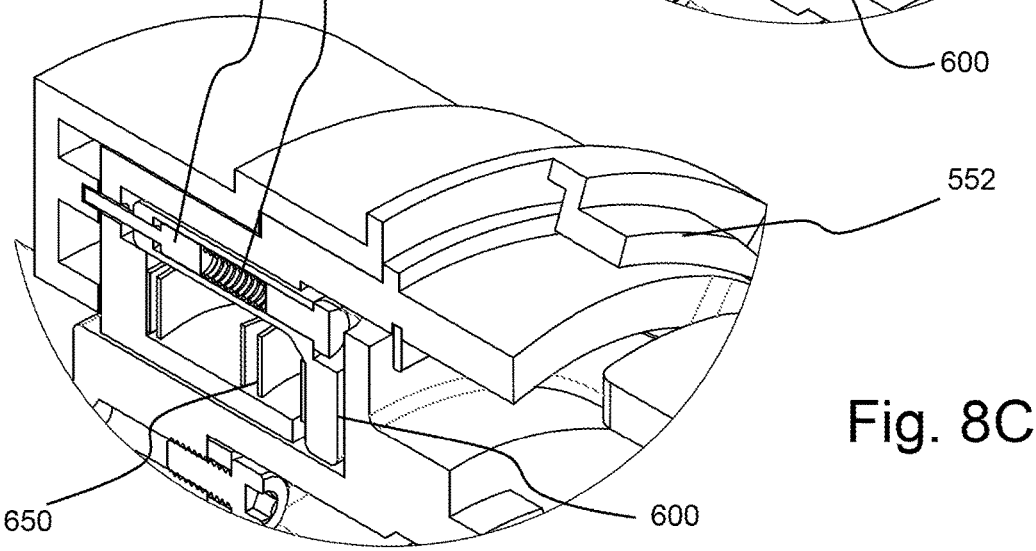
FIG. 8C illustrates an isometric view of the portion of the attachment system of FIG. 8A with the release ring thereof rotated to lift the spring clips.

Attachment system 500 as described above can further include one or more locking pins 570 as illustrated in FIG. 8A through 8C to interact with release ring 550 and hold release ring 550 in position once it had been rotated sufficiently to lift spring clips 540 over bayonet posts 110. Such locking pins 570 enable the user to let go of release ring 550 without needing to first remove alignment tool 200 from attachment point or interface 100, allowing the user to, for example, change their grip or get into a more comfortable position. The position of locking pins 570 may, for example, be dependent on the position of locking plate 600. If locking plate 600 is in the natural, uncompressed position (see FIG. 8A), locking pin(s) 570 are retracted. If locking plate 600 is in the compressed position (see FIG. 8B), one or more biasing members such as spring(s) 572 put pressure on locking pin(s) 570. When release ring 550 is rotated sufficiently to lift/deflect spring dips 540 as illustrated in FIG. 8C, one or more hole(s) or passages in release ring 550 align with the position of locking pin(s) 570, allowing them to extend into the holes thereby preventing release ring 550 from rotating and, as a result, holding the attachment system 500 in the "unlocked" configuration. As alignment tool 200 is removed from attachment point or interface 100, locking plate 600 will move to the uncompressed position, withdrawing the locking, pins, and allowing release ring 550 to freely rotate. At that point, torsion spring 560 will return release ring 550 to its initial position, lowering spring clips 540 and making the assembly of alignment tool 200 ready to secure to another attachment point or interface 100 as illustrated in FIG. 8A.

FIG. 9A through 9D illustrate another embodiment of an alignment tool 200a hereof wherein a release ring 550a of alignment tool 200a is engageable or interlockable with a touch point or gripping element 350a on scope mounting arm 310a of mount 300a of alignment tool 200a. In most respects, alignment tool 200a is similar in design and operation to alignment tool 200 and elements of alignment tool 200a are numbered similarly to like elements of alignment tool 200 with the addition a the designation "a" at the end of the reference number. In the illustrated embodiment, a radially extending engagement tab or flange 557a of release ring 550a is engageable with gripping element 350a. In the embodiment of FIGS. 9A through 9D, a relatively small engagement member, contact, or bump 558a (see FIGS. 9B and 9C) is provided to engage a cooperating engagement element (not shown) such as a recess in the gripping element 350a. Such a passive engagement system requires no extra moving parts. Cooperation/contact of engagement member 558a with the cooperating engagement element assists in locking or interlocking flange 557a and gripping element 350a together. The retention force for such coupling may be relatively low because it is undesirable for the act of repositioning the scope to accidentally drive release ring 550a.

FIGS. 9B and 9C illustrate rotation of mount 300a and scope 410a relative to attachment system 500a. FIG. 9D illustrates return of mount 300a and scope 410a to a zero position wherein extending flange 557a of release ring 550a engages or interlocks with gripping element 350a on scope mounting arm 310a so that the user may readily rotate the entire assembly of alignment tool 200a relative to one of the transmitter or receiver of system 10 (see FIG. 1) for attachment of alignment tool 200a thereto or for removal of alignment tool 200a therefrom. The engageable combination of flange 557a of release ring 550a with gripping element 350a thus facilitates the rotation of the full assembly of alignment tool 200a with a single hand (while, for example, a user grips both gripping element 350a and flange 557a) while also allowing rotation of mount 300a and scope 410a relative to attachment system 500a as described above.

FIGS. 10A through 10C illustrate another embodiment of an alignment tool 200b hereof wherein a release ring 550b of alignment tool 200b is engageable interlockable with a gripping member or interlocking member 350b attached to scope mounting arm 310b of mount 300b of alignment tool 200b. In most respects, alignment tool 200b is similar in design and operation to alignment tool 200 and elements of alignment tool 200b are numbered similarly to like elements of alignment tool 200 with the addition of the designation "b" at the end of the reference number. Similar to alignment tool 200a of FIGS. 9A through 9D, alignment tool 200b facilitates the ability of the user to rotate release ring 550b with the same hand that is grasping the scope mounting arm 310b. In the embodiment of alignment tool 200b, the user may engage release ring 550b regardless of the rotational position of scope mounting arm 310b. In the embodiment of alignment tool 200a of FIGS. 9A through 9D, scope mounting arm 310a must be aligned with the radially extending flange 557a of release ring 550a.

In the illustrated embodiment of FIG. 10A through 10C, release ring 550b includes a grooved surface 558b on a forward face including spaced grooves 558b' which interacts with interlocking member 350b in the form of a trigger. Interlocking member 350b is rotatably or pivotably connected to a mount 360b via a rod 362b which extends through mount 360b and through interlocking member 350b. Mount 360b is connected to mounting arm 310b. In a number of embodiments, the spacing between grooves 558b' on the forward face of release ring 550b is the same or approximately the same as the increments in which scope mounting arm 310b can rotate. Therefore, an interface member 354b of interlocking member 350b will always align to engage with one of the grooves 558b'. Squeezing trigger/interlocking member 350b (that is, moving a first end 352b thereof toward mounting arm 310b will force an interface member 354b on the opposite or second end of trigger/interlocking member 350b away from mounting arm 310b and into one of grooves 558b'. The interaction between interface member 354b and one of grooves 558b' will causes release nag 550b to rotate with scope mount 310b. A biasing device such as a spring (not shown) biases trigger/interlocking member 350b to its disengaged position when trigger/interlocking member 350b is released. Thus, the act of depressing trigger/interlocking member 350b locks release ring 550b and scope mounting arm 310b together. Releasing the trigger/interlocking member 350b will disengage release ring 550b and scope mounting arm 310b because the spring or other biasing member returns trigger/interlocking member 350b to its initial, disengaged position. Other controllable mechanisms or methods of actively engaging the release ring 550b and scope mounting arm 310b may alternatively be used. For example, one may rely on the friction between the end of a trigger/interlocking member and the forward face of the release ring.

The foregoing description and accompanying drawings set forth a number of representative embodiments at the present time. Various modifications, additions and alternative designs will, of course, become apparent to those skilled in the art in light of the foregoing teachings without departing front the scope hereof, which is indicated by the following claims rather than by the foregoing description. All changes and variations that fall within the meaning and range of equivalency of the claims are to be embraced within their scope.

What is claimed is:

1. An alignment tool for use in connection with an interface of either a transmitter or a receiver of an open path gas detection system, the interface of each of the transmitter and the receiver including one or more connectors, comprising:
   an optical system comprising a scope,
   an attachment system operatively connected to the optical system and comprising
      a body comprising one or more cooperating connectors which cooperate with the one or more connectors of the interface, wherein the body is rotatable about an axis thereof relative to the interface of one of the transmitter or the receiver in a first direction to bring the one or more cooperating connectors into connection with the one or more connectors of the interface, and one or more locking abutment elements which engage the one or more connectors of the interface after a predetermined amount of rotation of the body in the first direction, engagement of the one or more locking abutment elements with the one or more connectors of the interface forming a state of locked engagement wherein rotation of the body relative to the interface is prevented by the one or more locking abutment elements, and
      a release contact in rotatable connection with the body, wherein rotation of the release contact relative to the body in a second direction, opposite the first direction, causes the one or more locking abutment elements to disengage from the one or more connectors of the interface so that the body can be rotated in the second direction to remove the attachment system from connection with the interface.

2. The alignment tool of claim 1 further comprising a scope mounting arm in operative connection with the attachment system to which the scope is attached, the scope mounting arm being rotatable relative to the body of the attachment system when the attachment system is connected to the interface and the one or more locking abutment elements are in engagement with the one or more connectors of the interface.

3. The alignment tool of claim 2 wherein a predetermined level of force is required to rotate the scope mounting arm relative to the body of the attachment system and the predetermined level of force is sufficiently high such that the scope mounting arm can be grasped by a user and rotated to bring the attachment system into the state of locked engagement.

4. The alignment tool of claim 3 further comprising a locking plate attached to the body such that the locking plate cannot be rotated about the axis of the body relative to the body but can be translated in an axial direction relative to the body, the locking plate being biased into connection with a surface in operative connection with the scope mounting arm.

5. The alignment tool of claim 3 wherein the release contact comprises one or more mounting arm contacts, each of which can be placed in cooperative connection with the scope mounting arm to provide rotation of the release contact while gripping and rotating the scope mounting arm, and which allow rotation of the scope mounting arm relative to the body when the one or more mounting arm contacts are not in cooperative connection with the scope mounting arm.

6. The alignment tool of claim 2 wherein the one or more connectors of the interface comprise one or more extending bayonet posts and the one or more cooperating connectors comprise one or more channels formed in the body of the attachment system.

7. The alignment tool of claim 6 wherein the one or more locking abutment elements comprise one or more spring clips attached to the body, each of which comprise a passage therein to engage with and abut one of the one or more extending bayonet posts.

8. The alignment tool of claim 7 wherein the release contact comprises one or more abutment members which contact and flex the one or more spring clips when the release contact is rotated relative to the body in the second direction to disengage the passage of each of the one or more spring clips from the one or more extending bayonet posts.

9. The alignment tool of claim 8 wherein the release contact is formed as an annulus or ring which extends around a circumference of a section of the body.

10. The alignment tool of claim 2 wherein the release contact is biased into a position in which it does not cause the one or more locking abutment elements to disengage from the one or more connectors of the interface.

11. The alignment tool of claim 10 further comprising one or more retaining abutment members which engage the release contact after the release contact has been rotated in the second direction to disengage the one or more locking abutment elements from the one or more connectors of the interface to prevent the release contact from returning into a position in which it does not cause the one or more locking abutment elements to disengage from the one or more connectors of the interface until the body is rotated in the second direction a predetermined distance.

12. The alignment tool of claim 11 wherein the one or more retaining abutment members which engage the release contact comprise pins which are biased into engagement with the release contact when the release contact has been rotated in the second direction to disengage the one or more locking abutment elements from the one or more connectors of the interface.

13. A method of aligning at least one of a transmitter and a receiver of an open path gas detection system with the other of the transmitter and the receiver, each of the transmitter and the receiver including an interface including one or more connectors, comprising:
    providing an alignment tool comprising:
        an optical system comprising a scope, and
        an attachment system in operative connection with the optical system and comprising:
            a body comprising one or more cooperating connectors which cooperate with the one or more connectors of the interface of one of the transmitter or the receiver, wherein the body is rotatable about an axis thereof relative to the interface in a first direction to bring the one or more cooperating connectors into connection with the one or more connectors of the interface, and one or more locking abutment elements which engage the one or more connectors of the interface after a predetermined amount of rotation of the body in the first direction, engagement of the one or more locking abutment elements with the one or more connectors of the interface forming a state of locked engagement wherein rotation of the body relative to the interface is prevented by the one or more locking abutment elements, and
            a release contact in rotatable connection with the body, wherein rotation of the release contact relative to the body in a second direction, opposite the first direction, causes the one or more locking abutment elements to disengage from the one or more connectors of the interface so that the body can be rotated in the second direction to remove the attachment system from connection with the interface,
    attaching the alignment tool to the interface of the one of the transmitter or the receiver to form the state of locked engagement,
    using the optical system to align an optical axis of the one of the transmitter and the receiver to which the alignment tool is attached with the optical axis of the other of the transmitter and the receiver.

14. The method of claim 13 wherein the alignment tool further comprises a scope mounting arm in operative connection to the attachment system to which the scope is attached, the scope mounting arm being rotatable relative to the body of the attachment system when the attachment system is connected to the interface and the one or more locking abutment elements are in engagement with the one or more connectors of the interface.

15. The method of claim 14 wherein a predetermined level of force is required to rotate the scope mounting arm relative to the body of the attachment system and the predetermined level of force is sufficiently high such that the scope mounting arm can be grasped by a user and rotated to bring the attachment system into the state of locked engagement.

16. The method of claim 15 wherein the alignment tool further comprises a locking plate attached to the body such that the locking plate cannot be rotated about the axis of the body relative to the body but can be translated in an axial direction relative to the body, the locking plate being biased into connection with a surface in operative connection with the scope mounting arm.

17. The method of claim 15 wherein the release contact comprises one or more mounting arm contacts, each of which can be placed in cooperative connection with the scope mounting arm to provide rotation of the release contact while gripping and rotating the scope mounting arm, and which allow rotation of the scope mounting arm relative to the body when the one or more mounting arm contacts are not in cooperative connection with the scope mounting arm.

18. The method of claim 14 wherein the one or more connectors of the interface comprise one or more extending bayonet posts and the one or more cooperating connectors comprise one or more channels formed in the body of the attachment system.

19. The method of claim 18 wherein the one or more locking abutment elements comprise one or more spring clips attached to the body, each of which comprise a passage therein to engage with one of the one or more extending bayonet posts.

20. The method of claim 19 wherein the release contact comprises one or more abutment members which contact and flex the one or more spring clips when the release contact is rotated relative to the body in the second direction to disengage the passage of each of the one or more spring clips from the one or more extending bayonet posts.

21. The method of claim 20 wherein the release contact is formed as an annulus or ring which extends around a circumference of a section of the body.

22. The method of claim 14 wherein the release contact is biased into a position in which it does not cause the one or more locking abutment elements to disengage from the one or more connectors of the interface.

23. The method of claim 22 wherein the alignment tool further includes one or more retaining abutment members which engage the release contact after the release contact has been rotated in the second direction to disengage contact of the one or more locking abutment elements from the one or more connectors of the interface to prevent the release contact from returning into a position in which it does not cause the one or more locking abutment elements to disengage from the one or more connectors of the interface until the body is rotated in the second direction a predetermined distance.

24. The method of claim 23 wherein the one or more retaining abutment members which engage the release contact comprise pins which are biased into engagement with the release contact when the release contact has been rotated in the second direction to disengage the one or more locking abutment elements from the one or more connectors of the interface.

25. An attachment system for use in connection with an interface including one or more connectors, comprising:
    a body comprising
        one or more cooperating connectors which cooperate with the one or more connectors of the interface, wherein the body is rotatable about an axis thereof relative to the interface in a first direction to bring the one or more cooperating connectors into connection with the one or more connectors of the interface, and one or more locking abutment elements which engage the one or more connectors of the interface after a predetermined amount of rotation of the body in the first direction, engagement of the one or more locking abutment elements with the one or more connectors of the interface forming a state of locked engagement wherein rotation of the body relative to the interface is prevented by the one or more locking abutment elements, and
    a release contact in rotatable connection with the body, wherein rotation of the release contact relative to the body in a second direction, opposite the first direction, causes the one or more locking abutment elements to disengage from the one or more connectors of the interface so that the body can be rotated in the second direction to remove the attachment system from connection with the interface.

* * * * *